United States Patent [19]
Sato et al.

[11] 4,307,103
[45] Dec. 22, 1981

[54] DIHYDROPYRIDINE DERIVATIVE, PROCESSES FOR PREPARATION THEREOF AND PHARMACEUTICAL COMPOSITION COMPRISING THE SAME

[75] Inventors: Yoshinari Sato, Takaishi; Tsutomu Teraji, Osaka, both of Japan

[73] Assignee: Fujisawa Pharmaceutical Co., Ltd., Osaka, Japan

[21] Appl. No.: 70,098

[22] Filed: Aug. 27, 1979

[30] Foreign Application Priority Data

Sep. 8, 1978 [GB] United Kingdom ............... 36132/78

[51] Int. Cl.$^3$ .................... A61K 31/44; C07D 213/55; C07D 213/57
[52] U.S. Cl. .................................. 424/266; 546/272; 546/286; 546/287; 546/321
[58] Field of Search ............... 546/286, 287, 321, 272; 424/266

[56] References Cited

U.S. PATENT DOCUMENTS 3,974,278 8/1976 Bossert et al. ...................... 424/251

FOREIGN PATENT DOCUMENTS 2629892 1/1977 Fed. Rep. of Germany ...... 546/322

Primary Examiner—Alan L. Rotman
Attorney, Agent, or Firm—Dayton R. Stemple, Jr.

[57] ABSTRACT

This invention relates to a dihydropyridine derivative and a salt thereof. More particularly, it relates to a new dihydropyridine derivative and a pharmaceutically acceptable salt thereof which have vasodilating and antihypertensive activities, to processes for the preparation thereof, and to pharmaceutical composition comprising the same for therapeutical treatment of cardiovascular disorder and hypertension in human being.

13 Claims, No Drawings

DIHYDROPYRIDINE DERIVATIVE, PROCESSES FOR PREPARATION THEREOF AND PHARMACEUTICAL COMPOSITION COMPRISING THE SAME

BACKGROUND OF THE INVENTION

With regard to the states of the arts in this field, for example, the following dihydropyridine compounds are known.

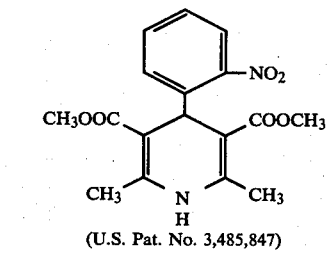
(A-1)

(U.S. Pat. No. 3,485,847)

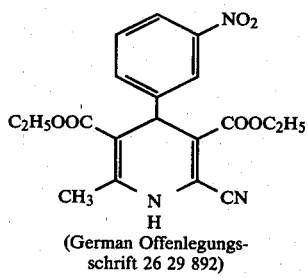
(A-2)

(German Offenlegungs-schrift 26 29 892)

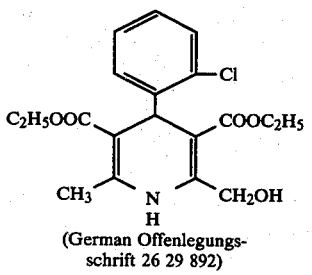
(A-3)

(German Offenlegungs-schrift 26 29 892)

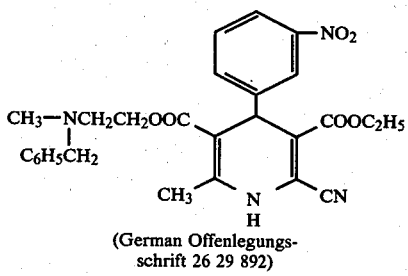
(A-4)

(German Offenlegungs-schrift 26 29 892)

One object of this invention is to provide the new and useful dihydropyridine derivative and the pharmaceutically acceptable salt thereof, which are structurally characterized in the substituent(s) at the third and/or sixth positions of the dihydropiridine nucleus and have stronger activity as compared with the known compounds, for example, as shown above, especially in anti-hypertensive activity.

Another object of this invention is to provide processes for the preparation of the dihydropyridine derivative and the salt thereof.

A further object of this invention is to provide an useful pharmaceutical composition comprising, as an active ingredient, said dihydropyridine derivative or the pharmaceutically acceptable salt thereof, which is useful as a vasodilator and anti-hypertensive agents, especially, anti-hypertensive agent.

Still further object of the present invention is to provide a therapeutical method for treatment of cardiovascular disorder such as coronary insufficiency, angina pectoris or myocardial infarction and hypertension.

The dihydropyridine derivative of this invention can be represented by the formula:

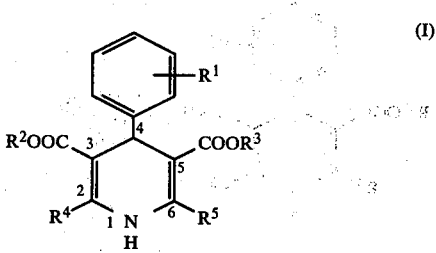
(I)

wherein
$R^1$ is nitro, halogen, lower alkoxycarbonyl, cyano, trihalo(lower)alkyl or phenyl,
$R^2$ is lower alkyl; [N-lower alkyl-N-haloar(lower)alkyl]amino(lower)alkyl; [N-lower alkyl-N-lower alkylar(lower)alkyl]amino(lower)alkyl; [N-lower alkyl-N-lower alkoxyar(lower)alkyl]amino(lower)alkyl; aroylamino(lower)alkyl, saturated N-containing heterocyclic(lower)alkyl, in which the N-containing heterocyclic moiety is always linked by the nitrogen atom to the lower alkyl moiety; heterocyclic-thio(lower)alkyl; lower alkanoyloxy(lower)alkyl; lower alkylthio(lower)alkyl; ar(lower)alkylthio(lower)alkyl; or arylthio(lower)alkyl,
$R^3$ is lower alkyl,
$R^4$ is lower alkyl and
$R^5$ is cyano, formyl, di(lower)alkoxymethyl, hydroxymethyl, halo(lower)alkanoyloxymethyl, lower alkanoyloxymethyl, lower alkoxyaroyloxymethyl, heterocycliccarbonyloxymethyl, lower alkanoyl(lower)alken-1-yl, halo(lower)alken-1-yl, cyano(lower)alken-1-yl, hydroxy(lower)alken-1-yl or lower alkyn1-yl,
provided that
when
$R^1$ is nitro, halogen or trihalo(lower)alkyl and $R^2$ is lower alkyl,
then $R^5$ is halo(lower)alkanoyloxymethyl, lower alkoxyaroyloxymethyl, heterocycliccarbonyloxymethyl, lower alkanoyl(lower)alken-1-yl, halo(lower)alken-1-yl, cyano(lower)alken-1-yl, hydroxy(lower)alken-1-yl or lower alkyn1-yl, and
when $R^1$ is cyano or lower alkoxycarbonyl and $R^2$ is lower alkyl,
then $R^5$ is halo(lower)alkanoyloxymethyl, lower alkanoyloxymethyl, lower alkoxyaroyloxymethyl, heterocycliccarbonyloxymethyl, lower alkanoyl(lower)alken-1-yl, halo(lower)alken-1-yl, cyano(lower)alken-1-yl, hydroxy(lower)alken-1-yl or lower alkyn-1-yl, With regard to the object compound of the above formula (I), it is to be understood that the compound (I) represents inclusively all of the possible optical and/or geometrical isomers due to the asymmetric carbon atom(s) and/or carbon-carbon double bond in the group for $R^5$ in the molecule of the compound (I), and accordingly such optical and/or geometrical isomers are also included within the scope of the present invention.

According to this invention, the object compound (I) can be prepared by the processes as illustrated by the following reaction schemes.

(1) Process 1

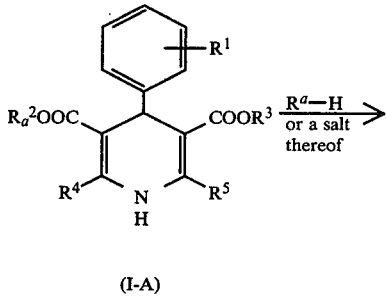

(I-A)

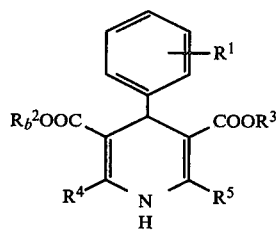

(I-1)

wherein
R¹, R³, R⁴ and R⁵ are each as defined before,
$R_a^2$ is halo(lower)alkyl,
$R_b^2$ is [N-lower alkyl-N-haloar(lower)alkyl]-amino(-lower)alkyl; [N-lower alkyl-N-lower alkylar(-lower)alkyl]amino(lower)alkyl; [N-lower alkyl-N-lower alkoxyar(lower)alkyl]amino(lower)alkyl; aroylamino(lower)alkyl; saturated N-containing heterocyclic(lower)alkyl, in which the N-containing heterocyclic moiety is always linked by the nitrogen atom to the lower alkyl moiety; or heterocyclic-thio(lower)alkyl and
$R^a$ is [N-lower alkyl-N-haloar(lower)alkyl]amino; [N-lower alkyl-N-lower alkylar(lower)alkyl]amino, N-lower alkyl-N-lower alkoxyar(lower alkyl)amino; aroylamino; saturated N-containing heterocyclic group; or heterocyclic-thio.

(2) Process 2

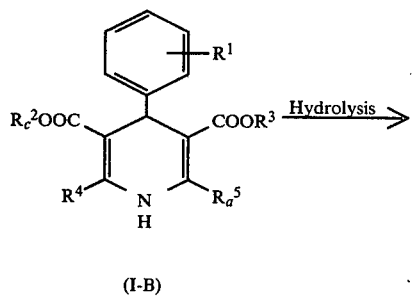

(I-B)

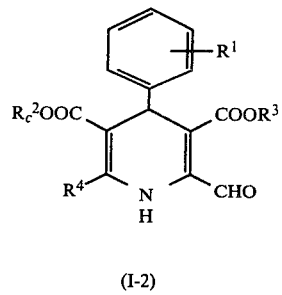

(I-2)

wherein
R¹, R³ and R⁴ are each as defined before,
$R_c^2$ is [N-lower alkyl-N-haloar(lower)alkyl]amino(-lower)alkyl; ]N-lower alkyl-N-lower alkylar(-lower)alkyl]amino(lower)alkyl; [N-lower alkyl-N-lower alkoxyar(lower)alkyl]amino(lower)alkyl; aroylamino(lower)alkyl; saturated N-containing heterocyclic-(lower)alkyl, in which the N-containing heterocyclic moiety is always linked by the nitrogen atom to the lower alkyl moiety; heterocyclicthio(lower)alkyl; lower alkanoyloxy(lower)alkyl; lower alkylthio(lower)alkyl, ar(lower)alkylthio(lower)alkyl or arylthio(lower)alkyl and
$R_a^5$ is di(lower)alkoxymethyl.

(3) Process 3

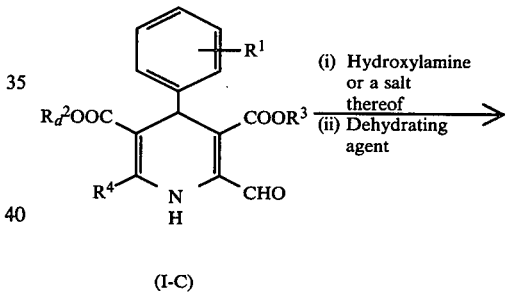

(I-C)

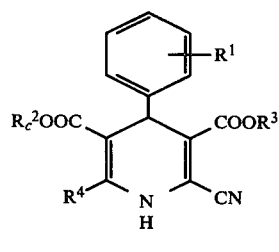

(I-3)

wherein
R¹, $R_c^2$, R³ and R⁴ are each as defined before, and
$R_d^2$ is [N-lower alkyl-N-haloar(lower)alkyl]amino(-lower)alkyl; [N-lower alkylN-lower alkylar(lower-)alkyl]amino(lower)alkyl; [N-lower alkyl-N-lower alkoxyar(lower)alkyl]amino(lower)alkyl; aroylamino(lower)alkyl; saturated N-containing heterocyclic-(lower)alkyl, in which the N-containing heterocyclic moiety is always linked by the nitrogen atom to the lower alkyl; heterocyclicthio(lower)alkyl; hydroxy(lower)alkyl; lower alkylthio(lower)alkyl; ar(lower)alkylthio(lower)alkyl, or arylthio(lower)alkyl.

(4) Process 4

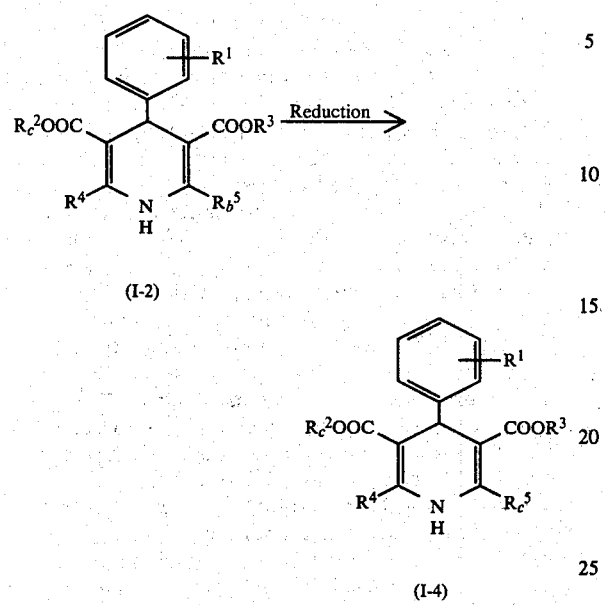

wherein
$R^1$, $R_c^2$, $R^3$ and $R^4$ are each as defined before,
$R_b^5$ is formyl or lower alkanoyl(lower)alken-1-yl, and
$R_c^5$ is hydroxymethyl or hydroxy(lower)alken-1-yl.

(5) Process 5

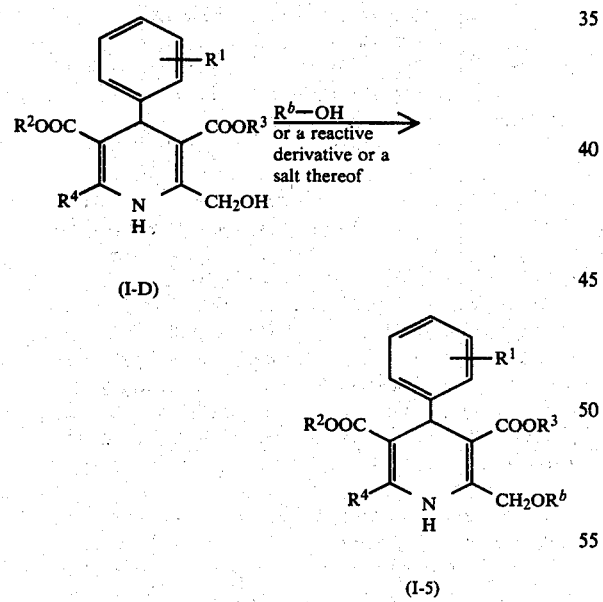

wherein
$R^1$, $R^2$, $R^3$ and $R^4$ are each as defined before, and
$R^b$ is lower alkanoyl, halo(lower)alkanoyl, lower alkoxyaroyl or heterocyclic-carbonyl, provided that when $R^1$ is nitro, halogen or trihalo(lower)alkyl and $R^2$ is lower alkyl, then $R^b$ is halo(lower)alkanoyl, lower alkoxyaroyl or heterocyclic-carbonyl, and when $R^1$ is cyano or lower alkoxycarbonyl, then $R^b$ is halo(lower)alkanoyl, lower alkanoyl, lower alkoxyaroyl or heterocycliccarbonyl.

(6) Process 6

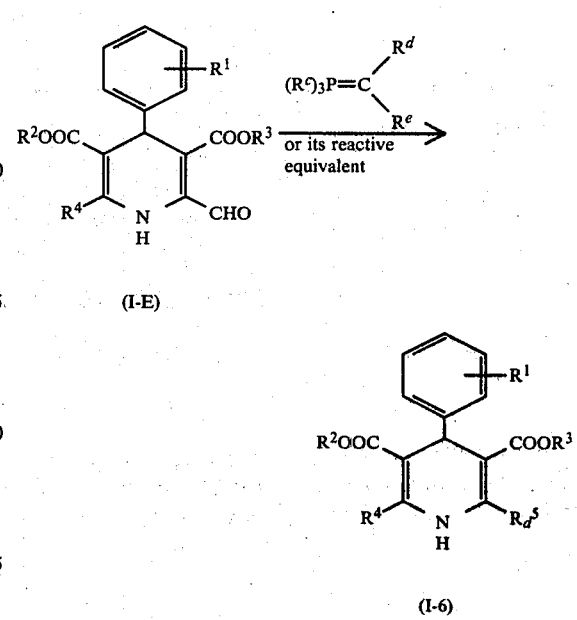

wherein
$R^1$, $R^2$, $R^3$ and $R^4$ are each as defined before,
$R_d^5$ is lower alkanoyl(lower)alken-1-yl, halo(lower)alken-1-yl or cyano(lower)alken-1-yl,
$R^c$ is aryl or lower alkyl,
$R^d$ is hydrogen or halogen, and
$R^e$ is lower alkanoyl, halogen or cyano.

(7) Process 7

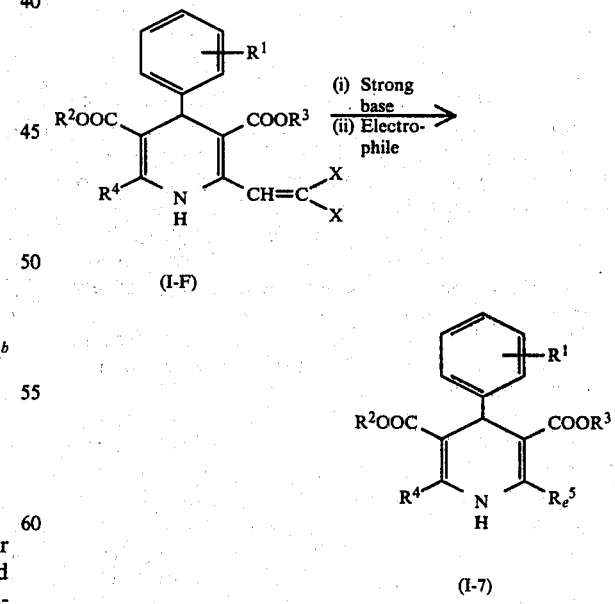

wherein
$R^1$, $R^2$, $R^3$ and $R^4$ are each as defined before,
$R_e^5$ is lower alkyn-1-yl, and
X is halogen.

Process 8

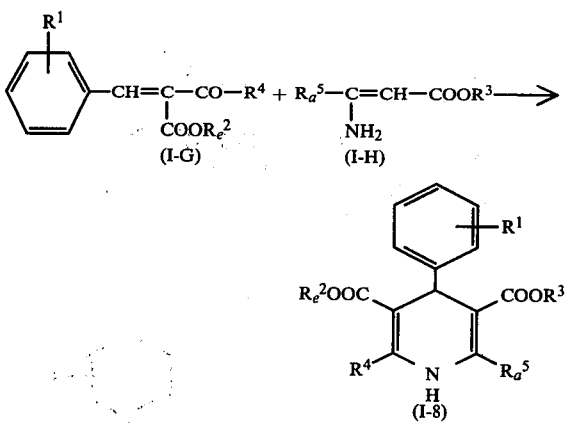

wherein $R^1$, $R^3$, $R^4$ and $R_a^5$ are each as defined before, and $R_e^2$ is lower alkylthio(lower)alkyl, ar(lower)alkylthio(lower)alkyl and arylthio(lower)alkyl.

Process 9

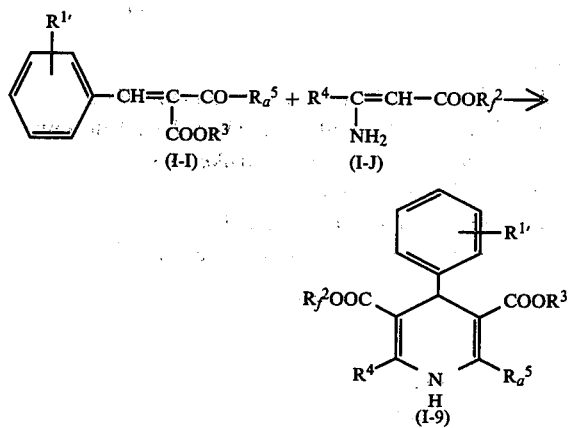

wherein $R^3$, $R^4$ and $R_a^5$ are each as defined before, $R^{1'}$ is phenyl and $R_f^2$ is lower alkyl.

Detailed explanation for the definitions used throughout this specification will be made and the suitable examples thereof will be illustrated in the following.

The term "lower" used in connection with all of the alkane, alkene and alkyne moieties is intended to mean 1 to 8 carbon atoms, preferably 1 to 6 carbon atoms, and more preferably 1 to 4 carbon atoms.

"Halogen" for $R^1$, $R^d$, $R^e$ and X includes fluorine, chlorine, bromine, iodine, and preferred one is chlorine and bromine.

"Lower alkoxycarbonyl" for $R^1$ can also be represented by the formula: —CO—O—(lower)alkyl, wherein the lower alkyl group includes monovalent radical of straight- and branched-chain(lower)alkanes. Suitable lower alkoxycarbonyl includes methoxycarbonyl, ethoxycarbonyl, propoxycarbonyl, isopropoxycarbonyl, butoxycarbonyl, t-butoxycarbonyl and the like, and more preferably methoxycarbonyl.

"Lower alkyl" for $R^2$, $R_f^2$, $R^3$, $R^4$ and $R^c$ includes a monovalent radical of straight- and branched-chain(lower)alkanes, and suitable lower alkyl group includes methyl, ethyl, propyl, isopropyl, butyl, isobutyl, t-butyl, pentyl, neopentyl, hexyl, heptyl, octyl and the like, more preferably $C_1$–$C_4$ alkyl group, and preferred one is methyl and ethyl.

"Trihalo(lower)alkyl" for $R^1$ preferably includes trihalomethyl such as trifluoromethyl or the like.

"[N-(lower)alkyl-N-haloar(lower)alkyl]amino(lower)alkyl" for $R^2$, $R_b^2$, $R_c^2$ and $R_d^2$ is intended to mean a lower alkyl which always bears [N-lower alkyl-N-haloar(lower)alkyl]amino group and particularly includes [N-lower alkyl-N-monohaloar(lower)alkyl]amino(lower)alkyl, preferred example of which may be [N-lower alkyl-N-monohalophenyl(lower)alkyl]amino(lower)alkyl such as N-lower alkyl-N-monohalobenzylamino(lower)alkyl [e.g. N-methyl-N-(2- or 3- or 4-chlorobenzyl)aminomethyl, 1- or 2-[N-methyl-N-(2- or 3- or 4-chlorobenzyl)amino]ethyl, 1- or 2-[N-ethyl-N-(2- or 3- or 4-chlorobenzyl)amino]ethyl, 1- or 2- or 3-[N-propyl-N-(2- or 3- or 4-chlorobenzyl)amino]propyl, 1- or 2-[N-methyl-N-(2- or 3- or 4-bromobenzyl)amino]ethyl, etc.; [N-(lower)alkylN-dihaloar(lower)alkylamino](lower)alkyl, preferred example of which may be [N-lower alkyl-N-dihalophenyl(lower)alkyl]amino(lower)alkyl such as N-lower alkylN-dihalobenzylamino(lower)alkyl [e.g. N-methyl-N-(2,3- or 3,4- or 2,4- or 3,5-dichlorobenzyl)aminomethyl, 1- or 2-[N-methyl-N-(2,3- or 3,5- or 2,4- or 3,4-dichlorobenzyl)amino]ethyl, 1- or 2-[N-ethyl-N-(2,3- or 3,4- or 2,4- or 3,5-dichlorobenzyl)amino]ethyl, 1- or 2- or 3[N-propyl-N-(2,3- or 3,4- or 2,4- or 3,5-dibromobenzyl)aminopropyl, etc.,] and the like, and particularly preferred one is 2-[N-methyl-N-(4-chlorobenzyl)amino]ethyl and 2-[N-methyl-N-(3,4-dichlorobenzyl)amino]ethyl.

"[N-lower alkyl-N-lower alkylar(lower)alkyl]amino(lower)alkyl" for $R^2$, $R_b^2$, $R_c^2$ and $R_d^2$ is intended to mean a lower alkyl which always bears [N-lower alkylN-lower alkylar(lower)alkyl]amino group and particularly includes [N-lower alkyl-N-lower alkylphenyl(lower)alkyl]amino(lower)alkyl such as N-lower alkyl-N-lower alkylbenzylamino(lower)alkyl (e.g. N-methyl-N-(2- or 3- or 4-methylbenzyl)aminomethyl, 1- or 2-[N-methyl-N-(2- or 3- or 4-methylbenzyl)amino]ethyl, 1- or 2- or 3-[N-propyl-N-(2- or 3- or 4-ethylbenzyl)amino]propyl, etc.) or the like, and particularly preferred one is 2-[N-methyl-N-(4-methylbenzyl)amino]ethyl.

"[N-lower alkyl-N-lower alkoxyar(lower)alkyl]amino(lower)alkyl" for $R^2$, $R_b^2$, $R_c^2$ and $R_d^2$ is intended to mean a lower alkyl which always bears [N-lower alkyl-N-lower alkoxyar(lower)alkyl]amino group and particularly includes [N-lower alkyl-N-lower alkoxyphenyl(lower)alkylamino](lower)alkyl such as N-lower alkyl-N-lower alkoxybenzylamino(lower)alkyl [e.g. N-methyl-N-(2- or 3- or 4-methoxybenzyl)aminomethyl, 1- or 2-[N-methyl-N-(2- or 3- or 4-methoxybenzyl)amino]ethyl, 1- or 2- or 3-[N-propyl-N-(2- or 3- or 4-ethoxybenzyl)amino]propyl, etc.,] or the like, and particularly preferred one is 2-[N-methyl-N-(4-methoxybenzyl)amino]ethyl.

"Aroylamino(lower)alkyl" for $R^2$, $R_b^2$, $R_c^2$ and $R_d^2$ is intended to mean a lower alkyl which always bears an aroylamino group, in which aroylamino group includes monobasic or dibasic aromatic carbonyl-amino and-imino groups including aroylamino(lower)alkyl such as benzamidomethyl, 1- or 2-benzamidoethyl, 1- or 2-toluamidoethyl or the like, and aroylimino(lower)alkyl such as phthaliminomethyl, 1- or 2-phthalimidoethyl, 1- or 2- or 3-phthalimidopropyl, or the like, and particularly preferred one is 2-phthalimidoethyl.

"Saturated N-containing heterocyclic-(lower)alkyl, in which the N-containing heterocyclic moiety is always linked by the nitrogen atom to the lower alkyl moiety" for $R^2$, $R_b{}^2$, $R_c{}^2$ and $R_d{}^2$ is particularly intended to mean a lower alkyl group which always bonds to 5 or 6-membered saturated N-containing heterocyclic moiety via the nitrogen atom thereof, in which the N-containing heterocyclic group may further contain at least one hetero-atom selected from two nitrogen atom and one oxygen atom. Suitable examples of 5 or 6-membered saturated N-containing heterocyclic-(lower)alkyl include morpholino(lower)alkyl such as morpholinomethyl, 1, or 2-morpholinoethyl, 1- or 2- or 3-morpholinopropyl, 1- or 2-, 3- or 4-morpholinobutyl, etc., (1-pyrrolidinyl)-(lower)alkyl such as (1-pyrrolidinyl)methyl, 1- or 2-(1-pyrrolidinyl)ethyl, 1- or 2- or 3-(1-pyrrolidinyl)propyl), etc., piperidino(lower)alkyl such as piperidino)methyl, 1- or 2-(piperidino)ethyl, 1- or 2- or 3-(piperidino)propyl, etc., 2-(1-methyl-4-piperazinyl)ethyl, etc., and the like, and preferred one is 2-morpholinoethyl.

"Heterocyclic" moiety of "heterocyclic-thio(lower)alkyl" for $R^2$, $R_b{}^2$, $R_c{}^2$ and $R_d{}^2$ and "heterocyclic-carbonyloxymethyl" for $R^5$ includes a heterocyclic group containing at least one hetero-atom selected from nitrogen, sulfur and oxygen atom, and may particularly include saturated or unsaturated, monocyclic or polycyclic heterocyclic group, and more particularly N-containing heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl, and its N-oxide, pyrimidinyl, pyrazinyl, pyridazinyl, triazolyl, (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.; saturated 3 to 6-membered heteromonocyclic group containing 1 to 4 nitrogen atoms (e.g., pyrrolidinyl, imidazolidinyl, piperidinyl, piperazinyl, etc.);
unsaturated condensed heterocyclic group containing 1 to 4 nitrogen atoms (e.g., indolyl, isoindolyl, indolizinyl, benzimidazolyl, quinolyl, isoquinolyl, indazolyl, benzotriazolyl, etc.);
unsaturated 3- to 6-membered heteromeoncyclic group containing 1 to 2 oxygen atoms and 1 to 3 nitrogen atoms, for example, oxazolyl, isoxazolyl, oxadiazolyl, (e.g., 1,2,4-oxadiazolyl, 1,3,4-oxadiazolyl, 1,2,5-oxadiazolyl, etc.), etc.;
saturated 3- to 6-membered heteromonocyclic group containing 1 to 2 oxygen atoms and 1 to 3 nitrogen atoms (e.g., morpholinyl, etc.);
unsaturated condensed heterocyclic group containing 1 to 2 oxygen atoms and 1 to 3 nitrogen atoms (e.g., benzoxazolyl, benzoxadiazolyl, etc.);
unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.), etc.;
saturated 3- to 6-membered heteromonocyclic group containing 1 to 2 sulfur atoms and 1 to 3 nitrogen atoms (e.g., thiazolidinyl, etc.);
unsaturated condensed heterocyclic group containing 1 to 2 sulfur atoms and 1 to 3 nitrogen atoms (e.g., benzothiazolyl, benzothiadiazolyl, etc.) and the like; wherein said heterocyclic group may have at least one suitable substituent such as lower alkyl (e.g., methyl, ethyl, propyl, isopropyl, butyl, isobutyl, pentyl, cyclopentyl, hexyl, cyclohexyl, etc.), or the like.

The "heterocyclic-thio(lower)alkyl" is particularly intended to mean a lower alkyl which always bears the above-exemplified heterocyclic-thio group, and preferred heterocyclic-thio(lower)alkyl is unsaturated 3 to 6 membered heteromonocyclic group containing 1 to 4 nitrogen atom(s) and having lower alkyl, and more preferred one is 1-methyl-1H-tetrazol-5-ylthiomethyl.

Preferred heterocyclic-carbonyloxymethyl containing above-exemplified heterocyclic group is unsaturated 3 to 6-membered heteromonocyclic group containing 1 to 4 nitrogen atoms, and more preferred one is nicotinoylmethyl.

"Lower alkylthio(lower)alkyl" for $R^2$, $R_c{}^2$, $R_d{}^2$ and $R_e{}^2$ includes lower alkylthiomethyl (e.g. methylthiomethyl, ethylthiomethyl, propylthiomethyl, butylthiomethyl, etc.), lower alkylthioethyl (e.g. methylthioethyl, ethylthioethyl, propylthioethyl, isopropylthioethyl, butylthioethyl, pentylthioethyl, hexylthioethyl, etc.), lower alkylthiopropyl (e.g. ethylthiopropyl, etc.), lower alkylthiobutyl (e.g. butylthiobutyl, etc.), and the like.

"Ar(lower)alkylthio(lower)alkyl" for $R^2$, $R_c{}^2$, $R_d{}^2$ and $R_e{}^2$ includes phenyl(lower)alkylthio(lower)alkyl such as benzylthio(lower)alkyl (e.g. benzylthiomethyl, benzylthioethyl, benzylthiopropyl, benzylthiobutyl, benzylthiopentyl, benzylthiohexyl, etc.) or the like.

"Arylthio(lower)alkyl" for $R^2$, $R_c{}^2$, $R_d{}^2$ and $R_e{}^2$ includes phenylthio(lower)alkyl such as phenylthiomethyl, phenylthioethyl, phenylthiopropyl, phenylthiobutyl, phenylthiopentyl, phenylthiohexyl or the like.

"Lower alkanoyloxy(lower)alkyl" for $R^2$ and $R_c{}^2$, in which the lower alkanoyl moiety can be referred to the same ones as illustrated hereinafter, preferably includes formyloxymethyl, acetoxymethyl, 1- or 2-formylethyl, 1- or 2-acetoxyethyl, 1- or 2-propionyloxyethyl, 1- or 2-butyryloxy ethyl, 1- or 2-valeryloxyethyl, 1- or 2- or 3-acetoxypropyl, 1- or 2- or 3- or 4-acetoxybutyl, and the like, and more preferred one is 2-formyloxyethyl and 2-acetoxyethyl.

"Halo(lower)alkyl" for $R_d{}^2$ is intended to mean halogen-substituted-(lower)alkyl group, in which the halogen is to be referred to those as illustrated before, and preferred examples thereof may be chloromethyl, 1- or 2-chloroethyl, 1- or 2 or 3-chloropropyl, 1- or 2- or 3- or 4-chlorobutyl, bromomethyl, 1- or 2-bromoethyl, and the like, and more preferred one is 2-chloroethyl.

"Hydroxy(lower)alkyl" for $R_d{}^2$ includes hydroxymethyl, 1- or 2-hydroxyethyl, 1- or 2- or 3-hydroxypropyl, 1- or 2- or 3- or 4-hydroxybutyl, and the like, and preferred one is 2-hydroxyethyl.

"Di(lower)alkoxymethyl" for $R^5$ and $R_a{}^5$ includes dimethoxymethyl, diethoxymethyl, dipropoxymethyl, diisopropoxymethyl, and the like, and preferred one is dimethoxymethyl and diethoxymethyl.

"Halo(lower)alkanoyloxymethyl" for $R^5$, in which the halogen and lower alkanoyl moieties are to be referred to ones as illustrated hereinbefore respectively, particularly includes fluoroacetoxymethyl, chloroacetoxymethyl, bromoacetoxymethyl, 2- or 3-chloropropionyloxymethyl, 2- or 3-bromopopionyloxymethyl, 2- or 3- or 4-chlorobutyryloxymethyl, and the like, and preferred one is 2-chloroacetoxymethyl.

Lower alkanoyl moiety of the "lower alkanoyloxymethyl" for $R^5$ may includes formyl, acetyl, propionyl, butyryl, valeryl, isovaleryl, or the like.

"Lower alkoxyaroyloxymethyl" for $R^5$ preferably includes mono- or di- or tri(lower)alkoxy aroyloxymethyl such as (mono-lower alkoxy)benzoyloxymethyl (e.g. 2- or 3- or 4-methoxybenzoyloxymethyl, 2- or 3- or 4-ethoxybenzoyloxymethyl, etc.), (di-lower alkoxy)benzoyloxymethyl (e.g. 2,3- or 3,4- or 2,4- or 3,5-dimethoxybenzoyloxymethyl, 2,3- or 3,4- or 2,4- or 3,5-diethoxybenzoyloxymethyl, etc.), (tri-lower alkoxy)benzoyloxymethyl (e.g. 2,3,4- or 3,4,5- or 2,3,5- or 2,4,5-trimethoxybenzoyloxymethyl, 2,3,4- or 3,4,5- or 2,3,5- or 2,4,5-triethoxybenzoyloxymethyl, etc.), and the like, and more preferred one is 3,4,5-trimethoxybenzoyloxymethyl.

"Lower alkanoyl(lower)alken-1-yl" for $R^5$, $R_b^5$ and $R_d^5$ preferably includes ones, in which the alken-1-yl moiety comprises 2 to 6 carbon atoms and preferred one is 2-formylvinyl, 2-acetylvinyl, propionylvinyl, and the like, and preferred one is 2-formylvinyl.

"Halo(lower)alken-1-yl" for $R^5$ and $R_d^5$ preferably includes mono- and di-halo(lower)alken-1-yl group, in which the lower alken-1-yl moiety comprises 2 to 6 carbon atoms and more preferred one is dihalo(lower)alken-1-yl such as 2,2-dichlorovinyl, 2,2-dibromovinyl, or the like.

"Cyano(lower)alken-1-yl" for $R^5$ and $R_d^5$ preferably includes ones, in which the alken-1-yl moiety comprises 2 to 6 carbon atoms and more preferred one is cyanovinyl.

"Hydroxy(lower)alken-1-yl" for $R^5$ and $R_c^5$ preferably includes ones, in which the alken-1-yl moiety comprises 3 to 6 carbon atoms, and particularly 3-hydroxy-1-(lower)alkenyl such as 3-hydroxy-1-propenyl, 3-hydroxy-1-butenyl, 3-hydroxy-1-pentenyl, and the like, and more preferred one is 3-hydroxy-1-propenyl.

"Lower alkyn-1-yl" for $R^5$ and $R_e^5$ preferably includes ones, in which the alkyn-1-yl moiety comprises 2 to 6 carbon atoms, and particularly ethynyl, 1-propynyl, 1-butynyl, 3-methyl-1-butynyl, 1-pentynyl, and the like, and more preferred one is ethynyl and 1-propynyl.

"[N-Lower alkyl-N-haloar(lower)alkyl]amino", "[N-lower alkyl-N-lower alkylar(lower)alkyl]amino", "[N-lower alkyl-N-lower alkoxyar(lower)alkyl]amino", "aroylamino", "a saturated N-containing heterocyclic group", "heterocyclic-thio" for $R^a$ are to be referred to the corresponding moieties of the groups as illustrated hereinbefore i.e., "[N-lower alkyl-N-haloar(lower)alkyl]amino(lower)alkyl", "[N-lower alkyl-N-lower alkoxyar(lower)alkyl]amino(lower)alkyl", "[N-lower alkyl-N-lower alkylar(lower)alkyl]amino(lower)alkyl", "aroylamino(lower)alkyl" "saturated N-containing heterocyclic-(lower)alkyl" and "heterocyclic-thio(lower)alkyl", respectively.

"Halo(lower)alkanoyl", "lower alkanoyl", "(lower alkoxy)aryl" and "heterocyclic-carbonyl" for $R^b$ and each to be referred to the corresponding acyl moieties of the groups as illustrated hereinbefore, i.e. "halo(lower)alkanoyloxymethyl", "lower alkanoyloxymethyl", "lower alkoxyaroyloxymethyl" and "heterocyclic-carbonyloxymethyl", respectively.

"Aryl" for $R^c$ includes phenyl, tolyl, xylyl, naphthyl, and the like, and preferred one is phenyl.

"Lower alkanoyl" for $R^e$ includes straight and branched ones such as formyl, acetyl, propionyl, butyryl, isobutyryl, valeryl, isovaleryl, hexanoyl or the like, and preferably straight one, and more preferably formyl and acetyl.

The starting compounds of this invention include known and new ones, and were prepared by the following reaction schemes or the similar method thereto.

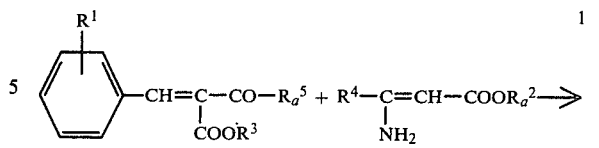

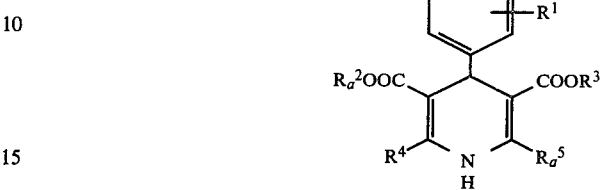

wherein $R^1$, $R_a^2$, $R^3$, $R^4$ and $R_a^5$ are each as defined before.

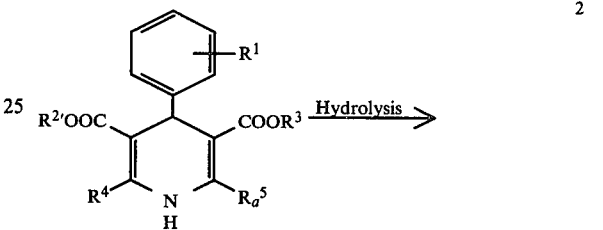

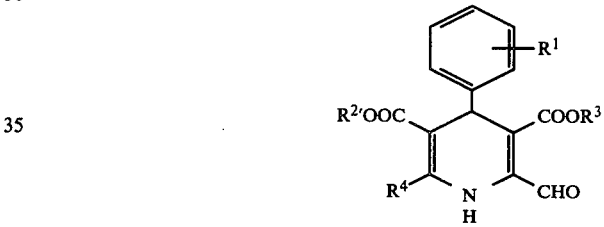

wherein $R^1$, $R^3$, $R^4$ and $R_a^5$ are each as defined before, and $R^{2'}$ is lower alkyl.

Processes for preparation of the dihydropyridine derivative (I) of this invention will be explained in details below.

(1) Process 1

This process relates to a method for preparing a compound (I-1) by reacting a compound (I-A) with a nucleophile of the formula: $R^a$-H, wherein $R^a$ is as defined before, or a salt thereof.

A salt of the nucleophile of the formula: $R^a$-H includes an alkali metal salt such as sodium salt, potassium salt, etc., an alkaline earth metal salt such as calcium salt, magnesium salt, etc., and the like.

This reaction can preferably be carried out in the presence of a base, suitable examples of which include an inorganic base such as an alkali metal hydroxide, carbonate, bicarbonate, hydride or amide (e.g. sodium hydroxide, potassium hydroxide, sodium carbonate, potassium carbonate, sodium bicarbonate, sodium hydride, sodium amide, etc.) or an organic base such as an alkali metal alkoxide (e.g. sodium methoxide, sodium ethoxide, potassium ethoxide, lithium methoxide, etc.), a salt of an organic acid (e.g. sodium acetate, potassium acetate, etc.), an amine or imine base (e.g. triethylamine, pyridine, picoline, N,N-dimethylaniline, N-methylpyrolidine, N-methylmorpholine, etc.) and the like.

Further, this reaction is preferably carried out in the presence of an alkali metal iodide such as lithium iodide, sodium iodide or the like in addition to the base. The reaction is usually carried out in a suitable solvent such as chloroform, methylene chloride, benzene, acetone, diethyl ether, tetrahydrofuran, dimethylformamide, methanol, ethanol propanol, isopropanol, water and other conventional solvent or an optional mixture thereof.

The reaction temperature is not restrictive, and the reaction is usually carried out at room temperature, or under warming or heating.

(2) Process 2

This process relates to a method for preparing a compound (I-2) by hydrolysing a compound (I-B).

The compound (I-B) can be prepared by the method as illustrated in the above Process 1.

In this process, the di(lower)alkoxymethyl group for $R_a^5$ of the compound (I-B) is transformed by hydrolysis into a formyl group.

Hydrolysis may be carried out in a conventional manner which is conventionally applied for cleavage of so-called an acetal function into the corresponding carbonyl function and preferably, for example, hydrolysis is carried out by an acidic hydrolysis, i.e. in the presence of an acid such as an inorganic acid (e.g. hydrochloric acid, sulfuric acid, etc.), an organic acid (e.g. formic acid, acetic acid, trifluoroacetic acid, p-toluenesulfonic acid, etc.) or an acidic ion-exchange resin.

This hydrolysis may be carried out in a suitable conventional solvent such as water, acetone, methyl ethyl ketone, dioxane, ethanol, methanol, N,N-dimethylformamide, or dimethylsulfoxide, an optional mixture thereof or a buffer solution thereof. The reaction temperature is not restrictive, and the reaction is usually conducted under cooling, at room temperature or under somewhat elevated temperature.

(3) Process 3

This process relates to a method for preparing a compound (I-3) by reacting a compound (I-C) with hydroxylamine or a salt thereof, and then reacting the resultant product with a dehydrating agent.

According to this process, the formyl group of the starting compound (I-C) is transformed into the hydroxyiminomethyl group (the first step), and in succession said group is transformed into the cyano group (the second step).

The compound (I-C) can be prepared according to the above Process 2.

Preferable salt of hydroxylamine may be a salt with an acid such as an inorganic acid (e.g. hydrochloric acid, sulfuric acid, etc.) or an organic acid (e.g. acetic acid, etc.).

(i) [Reaction of the first step]

This reaction is carried out in a usual manner as so-called oximation reaction, for example, in the presence of a catalyst such as an acid (e.g. hydrochloric acid, hydrobromic acid, sulfuric acid, formic acid, acetic acid, p-toluenesulfonic acid, boron trifluoride, silicon tetrachloride or titanium tetrachloride); in a basic condition brought about by a base, for example free hydroxylamine; or in an acidic or basic conventional buffer solution. The reaction is usually conducted in a suitable conventional solvent such as water, dioxane, ethanol, methanol or dimethylformamide or an optional mixture thereof, and when the above acid is in liquid, it can also be used as a solvent.

The reaction temperature is not restrictive, and the reaction is usually carried out under cooling, at room temperature or under somewhat elevated temperature.

The reaction product of the first step is subjected to the following second step with or without isolation.

(ii) [Reaction of the second step]

Suitable example of the dehydrating agent used in this step includes conventional organic or inorganic ones such as an inorganic acid (e.g. sulfuric acid, phosphoric acid, polyphosphoric acid, etc.), an organic acid (e.g. formic acid, acetic acid, trifluoroacetic acid, ethanesulfonic acid, p-toluenesulfonic acid, etc.), an organic acid anhydride including lower alkanoic anhydride, arenoic anhydride, etc., (e.g. acetic anhydride, benzoic anhydride, phthalic anhydride, etc.), an organic acid halide (e.g. acetyl chloride, benzoyl chloride, trichloroacetyl chloride, mesyl chloride, tosyl chloride, ethyl chloroformate, phenyl chloroformate, etc.); an inorganic halogen compound (e.g. thionyl chloride, phosphorus pentachloride, phosphorus oxychloride, phosphorus tribromide, stannic chloride, titanium tetrachloride, etc.); carbodiimide (e.g. N,N'-di-cyclohexylcarbodiimide, N-cyclohexyl-N'-morpholinoethylcarbodiimide, etc.), N,N'-carbonyldiimidazole; pentamethyleneketene-N-cyclohexylimine; ethoxyacetylene; 2-ethyl-7-hydroxyisoxazolium salt; other phosphorus compound (e.g. phosphorus pentoxide, polyphosphoric acid ethyl ester, triethylphosphate or phenylphosphate) and the like, or an optional mixture thereof. When an acid is used as the dehydrating agent, the reaction can also be conducted in the presence of its salt such as an alkali metal salt (e.g. sodium salt or potassium salt), and the like.

It is to be noted that the compound (I-3), wherein $R^1$, $R^3$ and $R^4$ are each as defined hereinabove and $R_c^2$ is lower alkanoyloxy(lower)alkyl, is to be prepared by treating the starting compound (I-C), wherein $R_d^2$ is hydroxy(lower)alkyl with the lower alkanoic acid anhydride mentioned above as the dehydrating agent.

This reaction is usually carried out in a conventional solvent such as diethyl ether, dimethylformamide, pyridine, acetic acid, formic acid, benzene, carbon tetrachloride, chloroform, methylene chloride, tetrahydrofuran, dioxane, and the like, and usually carried out at room temperature or under heating, but the reaction temperature is not restrictive to the above.

(4) Process 4

This process relates to a method for preparing a compound (I-4) by reducing the compound (I-2).

The reduction can be carried out in a conventional manner which can be applied for reduction of a formyl group into a hydroxymethyl group, and particularly, the reduction is conducted by using a reducing agent such as an alkali metal borohydride (e.g. lithium borohydride, sodium borohydride, potassium borohydride, sodium cyanoborohydride, etc.) or by catalytic reduction for which preferable catalyst may be palladium carbon, palladium chloride or rhodium carbon and the like. The reduction is usually carried out in a conventional solvent such as water, methanol, ethanol, isopropanol, dimethylformamide, tetrahydrofuran, etc., and the like. The reaction temperature is not restrictive, and the reaction is usually carried out under cooling, at room temperature or at somewhat elevated temperature. And, the method of reduction may optionally be selected according to the kind of the compound (I-2).

(5) Process 5

This process relates to a method for preparing a compound (I-5) by reacting a compound (I-D) with an acylating agent of the formula: $R^b$-OH, wherein $R^b$ is as defined before, or a reactive derivative or a salt thereof.

The reactive derivative of the acylating agent of the formula: $R^b$-OH includes:

an acid halide such as acid chloride, acid bromide or the like;

an acid anhydride such as a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g., methyl carbonate, ethyl carbonate, propyl carbonate, etc.), aliphatic carboxylic acid (e.g., pivalic acid, pentanoic acid, isopentanoic acid, 2-ethylbutyric acid, trichloroacetic acid, etc.), aromatic carboxylic acid (e.g., benzoic acid, etc.); a symmetrical acid anhydride; or the like.

an activated acid amide with a heterocyclic compound containing imino function such as imidazole, 4-substituted imidazole, dimethylpyrazole, triazole or tetrazole; an activated ester (e.g., cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.); and the like.

Suitable salts of the acylating agent include a salt with an inorganic base such as an alkali metal salt (e.g., sodium or potassium salt, etc.), an alkaline earth metal salt (e.g., calcium or magnesium salt, etc.), a salt with an organic base such as trimethylamine, triethylamine, and acid addition salt (e.g., hydrochloride, etc.), and the like. The suitable reactive derivative or salt of the acylating agent can optionally be selected from the above, according to the kinds of the acylating agent, the starting compound (I-D) and/or reaction condition (for example, solvent, reaction temperature, base, etc., as illustrated hereinbelow) to be used practically.

The reaction is preferably carried out in the presence of a base which can be referred to the same ones as those given in Process 1.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other organic solvent or an optional mixture thereof which does not adversely influence the reaction. Among these solvents, hydrophilic solvents may be used in a mixture with water. The reaction temperature is not restrictive and the reaction is usually carried out under cooling to at ambient temperature.

Further, when the acylating agent is used in a form of the free acid or its salt in this reaction, the reaction is preferably carried out in the presence of a condensing agent such as a carbodiimide compound (e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a ketenimine compound (e.g., N,N'-carbonylbis(2-methylimidazole), pentamethyleneketene-N-cyclohexylimine, diphenylketene-N-cyclohexylimine, etc.); an olefinic or acetylenic ether compound (e.g., ethoxyacetylene), β-chlorovinylethyl ether, a sulfonic acid ester of N-hydroxybenzotriazole derivative (e.g., 1-(4-chlorobenzenesulfonyloxy)-6-chloro-1H-benzotriazole, etc.), a phosphorus compound (e.g., trialkyl phosphite, ethyl polyphosphate, isopropyl polyphosphate, phosphoryl chloride, phosphorus trichloride, triphenylphosphine, etc.), thionyl chloride, oxalyl chloride, N-ethylbenzisoxazolium salt, N-ethyl-5-phenylisoxazolium-3'-sulfonate, a reagent (referred to as so-called "Vilsmeier reagent") formed by the reaction of an amide compound (e.g. dimethylformamide, dimethylacetamide, N-methylformamide, etc.) with a halogen compound (e.g. thionyl chloride, phosphoryl chloride, phosgene, etc.).

(6) Process 6

This process relates to a method for preparing a compound (I-6) by subjecting a compound (I-E) to so-called Wittig-type reaction with a phosphorane compound of the formula:

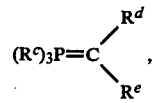

wherein $R^c$, $R^d$ and $R^e$ are each as defined before or its reactive equivalent.

The reaction equivalent of the phosphorane compound includes corresponding phosphonium salt which can be represented by the formula:

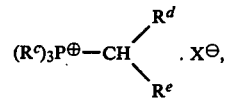

wherein $R^c$, $R^d$ and $R^e$ are each as defined above and X is halogen, prepared by reacting a phosphine compound of the formula: $(R^c)_3P$ with a halogen compound of the formula:

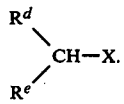

When the phosphonium salt in this reaction is used, the reaction is usually conducted in the presence of a strong base such as an alkali metal compound, for example, an alkoxide (e.g. sodium ethoxide, lithium ethoxide, potassium t-butoxide, etc.), a phenoxide (e.g. lithium phenoxide, etc.), an alkyl alkali metal compound (e.g. methyl lithium, butyl lithium, etc.), an aryl alkali metal compound (e.g., phenyl lithium, etc.), an aralkyl alkali metal compound (e.g., triphenylmethyl sodium, etc.), an alkali metal amide compound (e.g., N-methylanilino lithium, etc.) or the like.

This reaction is usually carried out in a suitable solvent such as methylene chloride, ethylene chloride, benzene, toluene and other conventional solvent or an optional mixture thereof.

The reaction temperature is not restrictive, and the reaction is usually carried out under cooling, at room temperature or somewhat elevated temperature.

It is to be noted that this reaction usually gives the cis- and trans geometrical isomers of the compound (I-6) due to the double bond to be formed, and these isomers are to be included within the scope of the object compound (I-6).

(7) Process 7

This process relates to a method for preparing a compound (I-7) by reacting a compound (I-F) with a strong base and then with electrophile.

The strong base preferably includes an alkali metal compound as exemplified in the foregoing Process 6, and more preferably an alkyl lithium (e.g. n-butyl lithium, etc.) an aryl lithium (e.g. phenyl lithium, etc.) and the like.

The electrophile includes a protic compound such as water, a lower alkyl halide (e.g. methyl iodide, ethyl bromide, etc.), or the like.

When water is used as the electrophile, the reaction is preferably conducted in the presence of an acid such as an inorganic acid (e.g. hydrochloric acid, sulfuric acid, etc.) and an organic acid (e.g. p-toluenesulfonic acid, formic acid, etc.).

This reaction is usually carried out in a suitable solvent such as tetrahydrofuran, diethyl ether, diisopropyl ether and other conventional solvent or an optional mixture thereof.

The reaction temperature is not restrictive, and the reaction is usually carried out under cooling.

In accordance with the present invention, the reaction product can be separated and isolated from the reaction mixture and purified by methods commonly used for this purpose, for instance, extraction with suitable solvent, chromatography, precipitation, recrystallization and so on.

Suitable examples of a salt of the dihydropyridine compound include a pharmaceutically acceptable salt such as an inorganic acid salt (e.g. hydrochloride, hydrobromide, phosphate, sulfate, etc.), an organic acid salt (e.g. formate, acetate, fumarate, maleate, etc.), or an amino acid salt (e.g. aspartate, glutamate, etc.).

(8) Process 8

This process relates to a method for preparing a compound (I-8) by reacting a compound (I-G) with an amino compound (I-H).

Each of the starting compounds (I-G) and (I-H) includes cis and trans isomers due to the double bond in their molecules, and both of such cis and trans isomers are equivalent in view of the compound (I-8), and therefore, each isomer and optional mixtures of the isomers of these starting compounds (I-G) and (I-H) are to be included within the scope of this process.

The reaction can be carried out at ambient temperature or under warming or heating. The reaction can be conducted in the absence of a solvent, but may be conducted in a suitable solvent such as benzene, toluene, xylene, chloroform, carbon tetrachloride, methylene chloride, ethylene chloride, methanol, propanol, butanol, water or other conventional solvents. The reaction can be preferably accelerated in the presence of an agent such as an acid (e.g. acetic acid), a base (e.g. pyridine or picoline) or in a conventional buffer solution. These agents act as a reaction accelerator and may also be used as a solvent when they are in liquid. The reactions can be also accelerated by warming or heating. The reaction condition may vary according to the kind of the reactants, solvent and/or other agent as mentioned above to be used.

(9) Process 9

This process relates to a method for preparing a compound (I-9) by reacting a compound (I-I) with an amino compound (I-J).

This process is substantially the same as Process 8, and accordingly can be conducted by reacting the compounds (I-I) and (I-J) in the same manner to those for the Process 8. That is, the same reaction conditions (e.g. reaction temperature, solvent, accelerator, etc.) and the same alternative reaction procedure as mentioned in the Process 8 are also applied to this process.

The compound (I) thus obtained frequently includes at least one pair of optical isomers due to the asymmetric carbon atoms of the fourth position of the 1,4-dihydropyridine nucleus, and of the lower alkyl groups and di(lower)alkoxymethyl for the groups in $R^2$, $R^3$ and $R^5$ and can exist as each optical isomer or a mixture thereof. A racemic compound can be resolved into each optical isomer by a conventional method for racemic resolution, such as a chemical resolution of the salts of the diastereomer with a conventional optically active acid (e.g. tartaric acid or camphor sulfonic acid, etc.).

As to utility of the object compound of this invention, it is to be noted that the compound (I) and a pharmaceutically acceptable salt thereof possess strong vasodilating activity and useful for therapeutical treatment in hypertension and cardiovascular diseases such as coronary insufficiency, angina pectoris or myocardial infarction.

Particularly, the compound (I), wherein $R^1$ is 3-nitro, $R^2$ is 2-[N-methyl-N-(4-chlorobenzyl)amino]ethyl or 2-[N-methyl-N-(3,4-dichlorobenzyl)amino]ethyl, $R^3$ is ethyl, $R^4$ is methyl and $R^5$ is cyano, has stronger vasodilating and anti-hypertensive activities, especially anti-hypertensive activity as compared with the known compounds as herein above.

In addition to the above utility, it is also to be noted that the compound (I), wherein $R^1$ is 3-nitro, $R^2$ is 2-[N-methyl-N-(4-chlorobenzyl)amino]ethyl or 2-[N-methyl-N-(3,4-dichlorobenzyl)amino]ethyl, $R^3$ is ethyl, $R^4$ is methyl and $R^5$ is diethoxymethyl or formyl, is useful not only as compound having vasodilating and anti-hypertensive activities but also as an intermediate for preparing the more potent vasodilating and anti-hypertensive agent of this invention as illustrated hereinabove.

For therapeutical purpose, the dihydropyridine derivative (I) is administered in daily dose of 0.1 to 500 mg, preferably 1 to 50 mg.

The pharmaceutical compositions of this invention comprise, as an active ingredient, the dihydropyridine derivative (I) or pharmaceutically acceptable salt thereof in an amount of about 0.01 mg. to about 500 mg., preferably about 0.1 mg. to about 250 mg. per dosage unit for oral and parenteral use.

One skilled in the art will recognize that the amount of the active ingredient in the dosage unit form will be determined by considering the activity of the ingredient as well as the size of the patient. The active ingredient may usually be formulated in a solid form such as tablet, granule, powder, capsule, troche, lozenge or suppository, or a suspension or solution form such as syrup, injection, emulsion, lemonade, etc. and the like. A pharmaceutical carrier or diluent includes solid or liquid non-toxic pharmaceutically acceptable substances. Examples of solid or liquid carriers or diluents are lactose, magnesium stearate, terra alba, sucrose, corn starch, talc, stearic acid, gelatin, agar, pectin, acacia, peanut oil, olive oil or sesame oil, cacao butter, ethyleneglycol or the other conventional ones. Similarly, the carrier or diluent may include a time delay material such as glyceryl monostearate, glyceryl disterarate, a wax and the like.

For the purpose of showing the utility of the compound (I), the pharmacological test results of same represented compounds will be shown as follows.

Hypotensive effect

Test Method

Five Wistar rats were used per group. Each animal was immobilized in a cage sized to the body. Blood pressure was measured at the femoral artery by means of a pressure transducer and recorded as electrical integrated values of mean arterial pressure, and the heart rate was determined by a pulse wave detector. Operation for the catheterization was performed under light anesthesia with ether. The test compound was administered orally 3 hrs after completion of the operation.

Test Compound

Compound A (reference compound): 2-(N-benzyl-N-methylamino)ethyl ester of 6-cyano-5-ethoxycarbonyl-2-methyl-4-(3-nitrophenyl)-1,4-dihydropyridine-3-carboxylic acid.
Compound B: 2-[N-(4-Chlorobenzyl)-N-methylamino]ethyl ester of 6-cyano-5-ethoxycarbonyl-2-methyl-4-(3-nitrophenyl)-1,4-dihydropyridine-3-carboxylic acid.
Compound C: Hydrochloride of 2-[N-(3,4-dichlorobenzyl)-N-methylamino]ethyl ester of 6-cyano-5-ethoxycarbonyl-2-methyl-4-(3-nitrophenyl)-1,4-dihydropyridine-3-carboxylic acid, hydrochloride.

Test Result

Mean values of Δ Maximum Decrease of blood pressure (mmHg) were shown in the following table.

| Compound | Dose | |
|---|---|---|
| | 1 mg/kg | 10 mg/kg |
| A | −11.0 ± 3.2 | −42.4 ± 0.9 |
| B | −29.2 ± 2.1 | −63.6 ± 3.5 |
| C | −25.6 ± 1.7 | −56.6 ± 0.8 |

The following Examples are given for the purpose of illustrating the syntheses of some specific compound of the present invention.

Preparation of the starting compound

Preparation (1) To a solution of 2-cyanobenzaldehyde (6.69 g) and 2-ethylthioethyl acetoacetate (10.5 g) in benzene (30 ml) was added eight times a solution of acetic acid (30 mg) and piperidine (28 mg) in benzene (0.2 ml) at intervals of half an hour with stirring, and the stirring was continued for 25 minutes. After adding benzene (50 ml) to the reaction mixture, the solution was washed with water until the neutral solution was obtained and then dried. The solvent was removed by distillation under reduced pressure to give an oil (16.28 g), which was chromatographed over silica gel (500 g) with chloroform as an eluent, and the fractions containing a desired compound were collected and evaporated to dryness under reduced pressure to give 2-ethylthioethyl 2-(2-cyanobenzylidene)acetoacetate (a mixture of cis and trans isomers) (16.28 g).

N.M.R.
δppm (CDCl$_3$): 1.21 (t, J = 7Hz), 1.27 (t, J = 7Hz) } (3H), 2.43 (s), 2.27 (s) } (3H), 2.63 (2H, t, J = 7Hz), 2.71 (2H, q, J = 7Hz), 4.25 (t, J = 7Hz), 4.37 (t, J = 7Hz) } (2H), 7.3–7.7 (4H, m), 7.73 (s), 7.81 (s) } (1H)

The following starting compounds were obtained in substantially the same manner as that of Preparation (1).

(2) 2-Benzylthioethyl 2-(2-cyanobenzylidene)acetoacetate (a mixture of cis and trans isomers).

N.M.R.
δppm (CDCl$_3$): 2.33 (s), 2.49 (s) } (3H), 2.4–2.9 (2H, m), 3.68 (s), 3.77 (s) } (2H), 4.28 (t, J = 7Hz), 4.36 (t, J = 7Hz) } (2H), 7.25–7.8 (9H, m), 7.82 (s), 7.91 (s) } (1H).

(3) 2-Phenylthioethyl 2-(2-cyanobenzylidene)acetoacetate (a mixture of cis and trans isomers).

N.M.R.
δppm (CDCl$_3$): 2.32 (s), 2.50 (s) } (3H), 3.08 (t, J = 7Hz), 3.23 (t, J = 7Hz) } (2H), 4.37 (t, J = 7Hz), 4.44 (t, J = 7Hz) } (2H), 7.15–7.8 (9H, m), 7.84 (s), 7.88 (s) } (1H).

(4) 2-Ethylthioethyl 2-(2-trifluoromethylbenzylidene)acetoacetate (a mixture of cis and trans isomers).

N.M.R.
δppm (CCl$_4$): 1.0–1.8 (3H, m), 2.1 (s), 2.4 (s) } (3H), 2.0–3.0 (4H, m), 4.0–4.4 (2H, m), 7.3–8.0 (5H, m)

Preparation of the object compound

EXAMPLE 1

(1) A mixture of 2-chloroethyl ester of 5-ethoxycarbonyl-6-diethoxymethyl-2-methyl-4-(3-nitrophenyl)-1,4-dihydropyridine-3-carboxylic acid (8.08 g.), N-(4-chlorobenzyl)-N-methylamine (3.80 g), triethylamine (2.47 g) and sodium iodide (0.24 g) in propyl alcohol (15 ml) was stirred at ambient temperature for 15 hours. After removal of the solvent from the reaction mixture, water and ethyl acetate were added to the residue. The organic layer was separated and washed with water. The washings and the remaining aqueous layer were combined and extracted with ethyl acetate. The combined extract was washed with a saturated aqueous solution of sodium chloride, dried and then evaporated to dryness under reduced pressure to give an oil (11.13 g) of 2-[N-(4-chlorobenzyl)-N-methylamino]ethyl ester of 5-ethoxycarbonyl-6-diethoxymethyl-2-methyl-4-(3-nitrophenyl)-1,4-dihydropyridine-3-carboxylic acid.

N.M.R.: δppm (CDCl$_3$): 2.19 (3H, s), 2.36 (3H, s), 3.43 (2H, s).

The following compounds were obtained in substantially the same manner as that of Example 1-1).

(2) 2-[N-(3,4-Dichlorobenzyl)-N-methylamino]ethyl ester of 5-ethoxycarbonyl-6-diethoxymethyl-2-methyl-4-(3-nitrophenyl)-1,4-dihydropyridine-3-carboxylic acid.

N.M.R.: δppm (CDCl$_3$): 2.19 (3H, s), 2.41 (3H, s), 3.41 (2H, s).

(3) 2-Phthalimidoethyl ester of 5-ethoxycarbonyl-6-diethoxymethyl-2-methyl-4-(3-nitrophenyl)-1,4-dihydropyridine-3-carboxylic acid, mp 99°–101° C.

(4) 2-Morpholinoethyl ester of 5-ethoxycarbonyl-6-diethoxymethyl-2-methyl-4-(3-nitrophenyl)-1,4-dihydropyridine-3-carboxylic acid, mp 107°–108.5° C.

(5) 2-(1-Methyl-1H-tetrazol-5-ylthio)ethyl ester of 5-ethoxycarbonyl-6-diethoxymethyl-2-methyl-4-(3-nitrophenyl)-1,4-dihydropyridine-3-carboxylic acid, mp 124.5°–126° C.

(6) 2-[N-Methyl-N-(4-methylbenzyl)amino]ethyl ester of 4-(2-cyanophenyl)-5-ethoxycarbonyl-6-diethoxymethyl-2-methyl-1,4-dihydropyridine-3-carboxylic acid.

N.M.R.: δppm (CDCl$_3$): 1.0–1.4 (9H, m), 2.13 (3H, s), 2.29 (3H, s), 2.33 (3H, s), 2.64 (2H, t, J=6.5 Hz), 3.41 (2H, s), 3.4–3.9 (4H, m), 4.13 (2H, q, J=6.5 Hz), 4.20 (2H, t, J=6.5Hz), 5.38 (1H, s) 6.24 (1H, s), 6.80 (1H, broad s), 7.0–7.6 (8H, m).

(7) 2-[N-(4-Methoxybenzyl)-N-methylamino[ethyl ester of 4-(2-cyanophenyl)-5-ethoxycarbonyl-6-diethoxymethyl-2-methyl-1,4-dihydropyridine-3-carboxylic acid.

N.M.R.: δppm (CDCl$_3$): 1.1–1.4 (9H, m), 2.15 (3H, s), 2.35 (3H, s), 2.65 (2H, t, J=6 Hz), 3.41 (2H, s), 3.5–4.3 (6H, m), 3.79 (3H, s), 5.38 (1H, s), 6.25 (1H, s), 6.5–7.6 (8H, m).

(8) 2-[N-(4-Chlorobenzyl)-N-methylamino]ethyl ester of 4-(2-cyanophenyl)-5-ethoxycarbonyl-6-diethoxymethyl-2-methyl-1,4-dihydropyridine-3-carboxylic acid.

N.M.R.: δppm (DCDl$_3$): 1.1–1.5 (9H, m), 2.17 (3H, s), 2.36 (3H, s), 2.66 (2H, t, J=6 Hz), 3.44 (2H, s), 3.4–4.1 (6H, m), 4.23 (2H, t, J=6 Hz), 5.41 (1H, s), 6.28 (1H, s), 6.83 (1H, broad s), 7.0–7.6 (8H, m).

(9) 2-[N-(3,4-Dichlorobenzyl)-N-methylamino]ethyl ester of 4-(2-cyanophenyl)-5-ethoxycarbonyl-6-diethoxymethyl-2-methyl-1,4-dihydropyridine-3-carboxylic acid.

N.M.R.: δppm (CDCl$_3$): 1.1–1.5 (9H, m), 2.15 (3H, s), 2.38 (3H, s), 2.66 (2H, t, J=6 Hz), 3.42 (2H, s), 3.4–4.1 (6H, m), 4.23 (2H, t, J=6 Hz), 5.38 (1H, s), 6.25 (1H, s), 6.81 (1H, broad s), 6.9–7.6 (7H, m).

EXAMPLE 2

(1) A mixture of 2-[N-(4-chlorobenzyl)-N-methylamino]ethyl ester of 5-ethoxycarbonyl-6-diethoxymethyl-2-methyl-4-(3-nitrophenyl)-1,4-dihydropyridine-3-carboxylic acid (11.13 g) and 6 N hydrochloric acid (11 ml) in acetone (120 ml) was stirred at ambient temperature for 2 hours. After removal of acetone from the reaction mixture, to the residue was added water. The aqueous solution was extracted twice with chloroform, and the combined extract was washed with an aqueous solution of sodium bicarbonate and then dried. After removal of the solvent under reduced pressure, the resultant reddish oily residue was pulverized and washed with diethyl ether. The powder was neutralized with an aqueous solution of sodium bicarbonate and extracted twice with ethyl acetate. The combined extract was washed with an aqueous solution of sodium chloride and then dried, followed by removing the solvent under reduced pressure to give an oil (8.54 g).

A part (2.05 g) of this oil was chromatographed over silica gel (60 g) and eluted with a mixture of benzene and ethyl acetate (5:1 by volume) as an eluent, and the fractions containing a desired compound were collected. The solvent was removed by distillation under reduced pressure to give oily 2-[N-(4-chlorobenzyl)-N-methylamino]ethyl ester of 5-ethoxycarbonyl-6-formyl-2-methyl-4-(3-nitrophenyl)-1,4-dihydropyridine-3-carboxylic acid (0.68 g). This oily product was crystallized from small amount of diisopropyl ether and recrystallized from the same solvent to provide the purified same product, mp 84°–84.5° C.

The following compounds were obtained in substantially the same manner as that of Example 2-1).

(2) 2-[N-(3,4-Dichlorobenzyl)-N-methylamino]ethyl ester of 5-ethoxycarbonyl-6-formyl-2-methyl-4-(3-nitrophenyl)-1,4-dihydropyridine-3-carboxylic acid, mp 104°–105° C.

(3) 2-Phthalimidoethyl ester of 5-ethoxycarbonyl-6-formyl-2-methyl-4-(3-nitrophenyl)-1,4-dihydropyridine-3-carboxylic acid, mp 168°–170° C.

(4) 2-Morpholinoethyl ester of 5-ethoxycarbonyl-6-formyl-2-methyl-4-(3-nitrophenyl)-1,4-dihydropyridine-3-carboxylic acid.

N.M.R. δppm (CDCl$_3$): 1.32 (3H, t, J=7 Hz), 2.2–2.7 (9H, m), 3.5–3.8 (4H, m), 4.0–4.4 (4H, m), 5.26 (1H, s), 7.2–8.2 (5H, m), 10.45 (1H, s).

(5) 2-(1-Methyl-1H-tetrazol-5-ylthio)ethyl ester of 5-ethoxycarbonyl-6-formyl-2-methyl-4-(3-nitrophenyl)-1,4-dihydropyridine-3-carboxylic acid, mp 158°–159.5° C.

(6) 2-[N-methyl-N-(4-methylbenzyl)amino]ethyl ester of 4-(2-cyanophenyl)-5-ethoxycarbonyl-6-formyl-2-methyl-1,4-dihydropyridine-3-carboxylic acid.

N.M.R. δppm (CDCl$_3$): 1.26 (3H, t, J=7.5 Hz), 2.13 (3H, s), 2.28 (3H, s), 2.38 (3H, s), 2.66 (2H, t, J=6 Hz), 3.43 (2H, s), 4.23 (2H, q, J=7.5 Hz), 4.23 (2H, t, J=6 Hz), 5.49 (1H, s), 6.9–7.7 (9H, m), 10.52 (1H, s).

(7) 2-[N-(4-Methoxybenzyl)-N-methylamino]ethyl ester of 4-(2-cyanophenyl)-5-ethoxycarbonyl-6-formyl-2-methyl-1,4-dihydropyridine-3-carboxylic acid.

N.M.R.: δppm (CDCl₃): 1.28 (3H, t, J=7 Hz), 2.17 (3H, s), 2.43 (3H, s), 2.68 (2H, t, J=6.5 Hz), 3.44 (2H, s), 3.80 (3H, s), 4.25 (2H, t, J=6.5 Hz), 4.27 (2H, q, J=7 Hz), 5.50 (1H, s), 6.7–7.7 (9H, m), 10.53 (1H, s).

(8) 2-[N-(4-Chlorobenzyl)-N-methylamino]ethyl ester of 4-(2-cyanophenyl)-5-ethoxycarbonyl-6-formyl-2-methyl-1,4-dihydropyridine-3-carboxylic acid.

N.M.R.: δppm (CDCl₃): 1.28 (3H, t, J=7.5 Hz), 2.17 (3H, s), 2.42 (3H, s), 2.67 (2H, t, J=6 Hz), 3.43 (2H, s), 4.23 (2H, t, J=6 Hz), 4.25 (2H, q, J=7.5 Hz), 5.48 (1H, s), 7.00 (1H, broad s), 7.1–7.7 (8H, m), 10.52 (1H, s).

(9) 2-[N-(3,4-Dichlorobenzyl)-N-methylamino]ethyl ester of 4-(2-cyanophenyl)-5-ethoxycarbonyl-6-formyl-2-methyl-1,4-dihydropyridine-3-carboxylic acid.

N.M.R.: δ ppm (CDCl₃): 1.28 (3H, t, J=6.5 Hz), 2.16 (3H, s), 2.44 (3H, s), 2.68 (2H, t, J=5.5 Hz), 3.42 (2H, s), 4.0–4.4 (4H, m), 5.47 (1H, s), 6.9–7.6 (8H, m), 10.53 (1H, s).

EXAMPLE 3

(1) A mixture of 2-[N-(4-chlorobenzyl)-N-methylamino]ethyl ester of 5-ethoxycarbonyl-6-formyl-2-methyl-4-(3-nitrophenyl)-1,4-dihydropyridine-3-carboxylic acid (6.5 g), hydroxylamine hydrochloride (1.0 g) and sodium acetate (1.48 g) in acetic acid (20 ml) was stirred at ambient temperature for an hour. To the reaction mixture was added acetic anhydride (4.29 g), and the mixture was stirred at ambient temperature for 2 hours and at 100° C. for additional 4 hours. After removal of the acetic acid from the reaction mixture, to the residue was added an aqueous solution of sodium bicarbonate and then extracted twice with ethyl acetate. The combined extract was washed with water, dried over magnesium sulfate and then evaporated to dryness under reduced pressure to give an oily residue (6.54 g), which was chromatographed over silica gel (200 g) and eluted with a mixture of benzene and ethyl acetate (5:1 by volume) as an eluent. The fractions containing a desired compound were collected and evaporated to dryness under reduced pressure to give an orange-yellowish oil of 2-[N-(4-chlorobenzyl)-N-methylamino]ethyl ester of 6-cyano-5-ethoxycarbonyl-2-methyl-4-(3-nitrophenyl)-1,4-dihydropyridine-3-carboxylic acid (3.15 g).

N.M.R.: δppm (CDCl₃): 1.28 (3H, t, J=7.5 Hz), 2.17 (3H, s), 2.40 (3H, s), 2.61 (2H, t, J=6 Hz), 3.46 (2H, s), 4.21 (2H, t, J=6 Hz), 4.27 (2H, q, J=7.5 Hz), 5.26 (1H, s), 7.3–8.2 (9H, m).

The product obtained above was transformed into its hydrochloride (2.31 g) by reacting said product with an ethanol solution of hydrogen chloride in a conventional manner, followed by pulverizing with diethyl ether and recrystallizing from an aqueous ethanol, mp 223°–225° C. (dec.).

The following compounds were obtained in substantially the same manner as that of Example 3-1).

(2) 2-[N-(3,4-Dichlorobenzyl)-N-methylamino]ethyl ester of 6-cyano-5-ethoxycarbonyl-2-methyl-4-(3-nitrophenyl)-1,4-dihydropyridine-3-carboxylic acid hydrochloride, mp 233.5°–234° C. (dec.).

(3) 2-Phthalimidoethyl ester of 6-cyano-5-ethoxycarbonyl-2-methyl-4-(3-nitrophenyl)-1,4-dihydropyridine-3-carboxylic acid, mp 158°–161° C.

(4) 2-Morpholinoethyl ester of 6-cyano-5-ethoxycarbonyl-2-methyl-4-(3-nitrophenyl)-1,4-dihydropyridine-3-carboxylic acid hydrochloride, mp 235° C. (dec.).

(5) 2-(1-Methyl-1H-tetrazol-5-ylthio)ethyl ester of 6-cyano-5-ethoxycarbonyl-2-methyl-4-(3-nitrophenyl)-1,4-dihydropyridine-3-carboxylic acid, mp 158°–160° C.

(6) 2-[N-Methyl-N-(4-methylbenzyl)amino]ethyl ester of 6-cyano-4-(2-cyanophenyl)-5-ethoxycarbonyl-2-methyl-1,4-dihydropyridine-3-carboxylic acid hydrochloride, mp 230° C. (dec.).

(7) 2-[N-(4-Methoxybenzyl)-N-methylamino]ethylester of 6-cyano-4-(2-cyanophenyl)-5-ethoxycarbonyl-2-methyl-1,4-dihydropyridine-3-carboxylic acid hydrochloride, mp 213°–214° C. (dec.).

(8) 2-[N-(4-Chlorobenzyl)-N-methylamino]ethyl ester of 6-cyano-4-(2-cyanophenyl)-5-ethoxycarbonyl-2-methyl-1,4-dihydropyridine-3-carboxylic acid hydrochloride, mp 232°–233° C. (dec.).

(9) 2-[N-(3,4-Dichlorobenzyl)-N-methylamino]ethyl ester of 6-cyano-4-(2-cyanophenyl)-5-ethoxycarbonyl-2-methyl-1,4-dihydropyridine-3-carboxylic acid hydrochloride, mp 240° C. (dec.).

(10) A solution of 2-hydroxyethyl ester of 5ethoxycarbonyl-6-formyl-2-methyl-4-(3-nitrophenyl)-1,4-dihydropyridine-3-carboxylic acid (5.22 g), hydroxylamine hydrochloride (1.08 g) and sodium acetate (1.48 g) in acetic acid (20 ml) was stirred at ambient temperature for an hour. To the reaction mixture was added acetic anhydride (5.79 g), and the mixture was stirred at ambient temperature for an hour and at 95°–100° C. for additional 3 hours. After the reaction mixture was allowed to cool to ambient temperature, the acetic acid was removed by distillation under reduced pressure. The residue was dissolved in ethyl acetate and washed with an aqueous solution of sodium bicarbonate and water, dried over magnesium sulfate and evaporated to dryness under reduced pressure to give an oil (6.17 g), which was chromatographed over silica gel (200 g) with a mixture of benzene and ethyl acetate (5:1 by volume) as an eluent. The fractions containing a desired compound were collected and evaporated to dryness under reduced pressure to give an orange-yellowish oil (3.23 g), which was crystallized from diethyl ether. The crude product (2.52 g) was recrystallized from diethyl ether to give yellowish crystals of 2-acetoxyethyl ester of 6-cyano5-ethoxycarbonyl-2-methyl-4-(3-nitrophenyl)-1,4-dihydropyridine-3-carboxylic acid (1.39 g), mp 114°–116° C.

EXAMPLE 4

(1) To a solution of 2-morpholinoethyl ester of 5-ethoxycarbonyl-6-formyl-2-methyl-4-(3-nitrophenyl)1,4-dihydropyridine-3-carboxylic acid (3.42 g) in ethanol (60 ml) was added portionwise sodium borohydride (0.27 g) under cooling at 0° C. over a period of half an hour with stirring, and the stirring was continued at the same temperature for 2 hours. After the reaction mixture was slightly acidified with 50% acetic acid, the ethanol was removed by distillation under reduced pressure below 35° C. To the residue was added water and then turned to be basic with an aqueous solution of sodium bicarbonate, and the separated oily substance was extracted twice with ethyl acetate. The combined extract was washed with a saturated aqueous solution of sodium chloride and dried over magnesium sulfate to give a foamy oil (3.25 g), which was allowed to stand in a refrigerator over night and triturated with diethyl ether to give a crude pale yellowish powder (2.56 g) of 2-morpholinoethyl ester of 5-ethoxycarbonyl-6-hydroxymethyl-2-methyl-4-(3-nitrophenyl)-1,4-dihydropyridine-3-carboxylic acid.

Yellowish powder (0.14 g) of the same product was recovered from the filtrate. The combined powder was recrystallized from methanol to give a purified yellowish needles of the same product (1.69 g), mp 104°–106° C.

The following compound was obtained in substantially the same manner as that of Example 4-1).

(2) Isopropyl ester of 4-(2-chlorophenyl)-6-(3-hydroxy-1-propenyl)-5-methoxycarbonyl-2-methyl-1,4-dihydropyridine-3-carboxylic acid, mp 107°–110° C.

(3) 2-[N-Methyl-N-(4-methylbenzyl)amino]ethyl ester of 4-(2-cyanophenyl)-5-ethoxycarbonyl-6-hydroxymethyl-2-methyl-1,4-dihydropyridine-3-carboxylic acid, mp 174°–176° C.

(4) 2-[N-(4-Methoxybenzyl)-N-methylamino]ethyl ester of 4-(2-cyanophenyl)-5-ethoxycarbonyl-6-hydroxymethyl-2-methyl-1,4-dihydropyridine-3-carboxylic acid, mp 161°–163° C.

(5) 2-[N-(4-Chlorobenzyl)-N-methylamino]ethyl ester of 4-(2-cyanophenyl)-5-ethoxycarbonyl-6-hydroxymethyl-2-methyl-1,4-dihydropyridine-3-carboxylic acid, mp 158°–159° C.

(6) 2-[N-(3,4-Dichlorophenyl)-N-methylamino]ethyl ester of 4-(2-cyanophenyl)-5-ethoxycarbonyl-6-hydroxymethyl-2-methyl-1,4-dihydropyridine-3-carboxylic acid, mp 167°–169° C.

EXAMPLE 5

(1) To a solution of isopropyl ester of 6hydroxymethyl-5-methoxycarbonyl-4-(2-methoxycarbonylphenyl)-2-methyl-1,4-dihydropyridine-3-carboxylic acid (2.60 g) in pyridine (20 ml) was added dropwise a solution of acetyl chloride (0.83 g) in methylene chloride (10 ml) under cooling at 0° C. over a period of a half an hour with stirring, and the stirring was continued at the same temperature for 1.3 hours. After removal of the solvent, the residue was dissolved in ethyl acetate and washed with 1 N hydrochloride acid and water, dried over magnesium sulfate and evaporated to dryness under reduced pressure to give an oil (3.10 g), which was crystallized from diethyl ether. The yellowish crystals (2.29 g) were recrystallized from methanol (9 ml) to provide yellowish crystals (1.80 g) of isopropyl ester of 6-acetoxymethyl-5-methoxycarbonyl-4-(2-methoxycarbonylphenyl)-2-methyl-1,4-dihydropyridine-3-carboxylic acid, mp 123°–124° C.

The following compounds were obtained in substantially the same manner as that of Example 5-1).

(2) Diethyl ester of 6-chloroacetoxymethyl-2-methyl-4-(3-nitrophenyl)-1,4-dihydropyridine-3,5-dicarboxylic acid, mp 111.9°–113° C.

(3) Diethyl ester of 6-(3,4,5-trimethoxybenzoyloxymethyl)-2-methyl-4-(3-nitrophenyl)-1,4-dihydropyridine-3,5-dicarboxylic acid, mp 152°–153.2° C.

(4) Diethyl ester of 6-nicotinoyloxymethyl-2-methyl-4-(3-nitrophenyl)-1,4-dihydropyridine-3,5-dicarboxylic acid, mp 139°–140° C.

EXAMPLE 6

(1) To a solution of 2-triphenylphosphoranylideneacetaldehyde (1.9 g) in methylene chloride (15 ml) was added dropwise little by little a solution of isopropyl ester of 4-(2-chlorophenyl)-6-formyl-5-methoxycarbonyl-2-methyl-1,4-dihydropyridine-3-carboxylic acid (2.14 g) in methylene chloride (25 ml) with stirring over a period of 50 minutes, and the stirring was continued at ambient temperature for an hour. After removal of the methylene chloride from the reaction mixture, the residue was dissolved in benzene (10 ml) and subjected to column chromatography over silica gel (120 g). Elution was carried out with a mixture of benzene and ethyl acetate (10:1 by volume), and fractions containing a desired compound were collected and evaporated to dryness under reduced pressure to give orange needles of isopropyl ester of 4-(2-chlorophenyl)-6-(2-formylvinyl)-5-methoxycarbonyl-2-methyl-1,4-dihydropyridine-3-carboxylic acid (1.0 g), mp 179°–180.5° C.

The same product (0.1 g) was recovered from the mother liquor. Total yield was 1.1 g.

The following compounds were obtained in substantially the same manner as that of Example 6-1).

(2) Isopropyl ester of 6-(2-acetylvinyl)-4-(2-chlorophenyl)-5-methoxycarbonyl-2-methyl-1,4-dihydropyridine-3-carboxylic acid, mp 154°–156° C.

(3) Isopropyl ester of 4-(2-chlorophenyl)-6-(2-cyanovinyl)-5-methoxycarbonyl-2-methyl-1,4-dihydropyridine-3-carboxylic acid, mp 159°–161.5° C.

(4) A mixture of isopropyl ester of 4-(2-chlorophenyl)-6-formyl-5-methoxycarbonyl-2-methyl-1,4-dihydropyridine-3-carboxylic acid (0.472 g), triphenylphosphine (0.787 g) and carbon tetrachloride (2 ml) was refluxed for 50 minutes under heating. After cooling, to the reaction mixture was added chloroform to dissolve it, washed three times with water and then evaporated to dryness to give a dark red-brown oil (1.74 g), which was chromatographed over silica gel (87 g) with a mixture of benzene and ethyl acetate (20:1 by volume) as an eluent. The fractions containing a desired compound were collected and evaporated to dryness under reduced pressure to give a resinous substance, which was triturated with diethyl ether and collected by filtration. These crystals were recrystallized from diisopropyl ether to give yellowish needles of isopropyl ester of 4-(2-chlorophenyl)-6-(2,2,-dichlorovinyl)-5-methoxycarbonyl-2-methyl-1,4-dihydropyridine-3-carboxylic acid, mp 153°–154° C.

The following compound was obtained in the same manner as that of Example 6-4).

(5) Isopropyl ester of 6-(2,2-dibromovinyl)-4-(2-chlorophenyl)-5-methoxycarbonyl-2-methyl-1,4-dihydropyridine-3-carboxylic acid, mp 155°–157° C.

EXAMPLE 7

(1) To a solution of isopropyl ester of 6-(2,2-dibromovinyl)-4-(2-chlorophenyl)-5-methoxycarbonyl2-methyl-1,4-dihydropyridine-3-carboxylic acid (1.65 g) in tetrahydrofuran (30 ml) was added dropwise a solution of n-butyllithium (5.95 ml) in tetrahydrofuran (8 ml) at −27° to −21° C. with stirring over a period of 20 minutes, and the stirring was continued for additional 20 minutes at the same temperature. To the reaction mixture was added diluted hydrochloric acid and then the tetrahydrofuran was removed therefrom. The residue was dissolved in ethyl acetate and washed three times with water, dried and then evaporated to dryness under water, dried and then evaporated to dryness under reduced pressure. The residual reddish oil was triturated with diisopropyl ether and allowed to stand for half an hour to provide an orange-yellowish powder (0.55 g), and the same powder (0.42 g) was recovered from the filtrate. The combined powder (0.97 g) was recrystallized from methanol to give orange-yellowish crystals of isopropyl ester of 6-ethynyl-4-(2-chlorophenyl)-5-methoxycarbonyl-2-methyl-1,4-dihydropyridine-3-carboxylic acid (0.47 g). The same product (0.11 g) was recovered from the mother liquor. Total yield was 0.58 g. Additional recrystallization from methanol gave the purified same object compound, mp 172°–173.5° C.

(2) To a solution of isopropyl ester of 6-(2,2-dibromovinyl)-4-(2-chlorophenyl)-5-methoxycarbonyl-2-methyl-1,4-dihydropyridine-3-carboxylic acid (747.2 mg) in tetrahydrofuran (16 ml) was added dropwise a solution of n-butyllithium (2.7 ml) in tetrahydrofuran (4 ml) under cooling at −20° C. with stirring over a period of 15 minutes, and the stirring was continued at the same temperature for about 25 minutes. To the resultant mixture was added dropwise a solution of methyl iodide (198.7 mg) in tetrahydrofuran (1 ml) under cooling at −22° to −20° C. with stirring over a period of 5 minutes and the stirring was continued at the same temperature for an hour and for additional half an hour while the reaction temperature gradually elevated from −20° C. to −10° C. Diluted hydrochloric acid was added to the reaction mixture and the tetrahydrofuran was removed by distillation therefrom under reduced pressure. The resultant residue was extracted with ethyl acetate, and the extract was washed three times with water, dried and then evaporated to dryness to give an oil (0.63 g), which was chromatographed over silica gel (63 g) with a mixture of benzene and ethyl acetate (10:1 by volume) as an eluent. The fractions containing a desired compound were collected and evaporated to dryness to give a mixture (450 mg) of isopropyl ester of 6-ethynyl-4-(2-chlorophenyl)-5-methoxycarbonyl-2-methyl-1,4-dihydropyridine-3-carboxylic acid and isopropyl ester of 6-(1-propynyl)-4-(2-chlorophenyl)-5-methoxycarbonyl-2-methyl-1,4-dihydropyridine-3-carboxylic acid (2:1 by N.M.R.). Physical constant of the latter is as follows.

N.M.R.: $\delta$ppm (CDCl$_3$): 1.05 (3H, s), 3.66 (3H, s), 4.97 (1H, heptet, J=6.5 Hz), 5.42 (1H, s).

EXAMPLE 8

The following compounds were obtained in substantially the same manner as that of Example 1-1).

(1) 2-[N-(3,4-Dichlorobenzyl)-N-methylamino]ethyl ester of 5-ethoxycarbonyl-6-diethoxymethyl-2-methyl-4-(2-trifluoromethylphenyl)-1,4-dihydropyridine-3-carboxylic acid.

N.M.R.: $\delta$ppm (CDCl$_3$): 1.07–1.36 (9H, m), 2.14 (3H, s), 2.33 (3H, s), 2.57 (2H, t, J=6 Hz), 3.39 (2H, s), 3.4–4.4 (8H, m), 5.62 (1H, broad s), 6.11 (1H, s), 6.72 (1H, s), 7.0–7.7 (7H, m).

(2) 2-[N-(4-Chlorobenzyl)-N-methylamino]ethyl ester of 4-(2-trifluoromethylphenyl)-5-ethoxycarbonyl-6-diethoxymethyl-2-methyl-1,4-dihydropyridine-3-carboxylic acid.

N.M.R.: $\delta$ppm (CDCl$_3$): 1.16 (t, J=6.5 Hz), (9H), 2.14 (3H, s), 1.23 (t, J=7 Hz) 2.30 (3H, s), 2.57 (2H, t, J=6 Hz), 3.42 (s), (10H), 5.53–5.65 (1H, m), 3.3–4.3 (m) 6.09 (1H, s), 6.68 (1H, broad), 7.1–7.6 (8H, m).

EXAMPLE 9

The following compounds were obtained in substantially the same manner as that of Example 2-1).

(1) 2-[N-(3,4-Dichlorobenzyl)-N-methylamino]ether ester of 5-ethoxycarbonyl-6-formyl-2-methyl-4-(trifluoromethylphenyl)-1,4-dihydropyridine-3-carboxylic acid.

N.M.R.: $\delta$ppm (CDCl$_3$): 1.23 (3H, t, J=7.5 Hz), 2.17 (3H, s) 2.43 (3H, s), 2.60 (2H, t, J=6.5 Hz) 3.43 (2H, s), 3.95–4.5 (4H, m), 5.71 (1H, broad s), 7.0 (1H, m), 7.1–7.8 (7H, m), 10.29 (1H, s).

(2) Isopropyl ester of 4-(2-biphenylyl)-6-formyl-5-methoxycarbonyl-2-methyl-1,4-dihydropyridine-3-carboxylic acid, mp 121.5°–123.5° C.

(3) 2-Ethylthioethyl ester of 4-(2-cyanophenyl)-5-ethoxycarbonyl-6-formyl-2-methyl-1,4-dihydropyridine-3-carboxylic acid, mp 98°–100° C.

EXAMPLE 10

The following compounds were obtained in substantially the same manner as that of Example 3-1).

(1) 2-[N-(3,4-Dichlorobenzyl)-N-methylamino]ethyl ester of 6-cyano-5-ethoxycarbonyl-2-methyl-4-(2-trifluoromethylphenyl)-1,4-dihydropyridine-3-carboxylic acid hydrochloride, mp 228°–229° C. (dec.).

(2) Isopropyl ester of 4-(2-biphenylyl)-6-cyano-5-methoxycarbonyl-2-methyl-1,4-dihydropyridine-3-carboxylic acid, mp 164.1°–165.8° C.

(3) 2-Ethylthioetyl ester of 6-cyano-4-(2-cyanophenyl)-5-ethoxycarbonyl-2-methyl-1,4-dihydropyridine-3-carboxylic acid, mp 125°–127° C.

EXAMPLE 11

The following compounds were obtained in substantially the same manner as that of Example 4-1).

(1) 2-[N-(3,4-Dichlorobenzyl)-N-methylamino]ethyl ester of 5-ethoxycarbonyl-6-hydroxymethyl-2-methyl-4-(2-trifluoromethylphenyl)-1,4-dihydropyridine-3-carboxylic acid, mp 135°–137° C.

(2) Isopropyl ester of 4-(2-biphenylyl)-6-hydroxymethyl-5-methoxycarbonyl-2-methyl-1,4-dihydropyridine-3-carboxylic acid, mp 131.5°–132° C.

(3) 2-Ethylthioethyl ester of 4-(2-cyanophenyl)-5-ethoxycarbonyl-6-hydroxymethyl-2-methyl-1,4-dihydropyridine-3-carboxylic acid, mp 85°–87° C.

EXAMPLE 12

The following compounds were obtained in substantially the same manner as that of Example 2-1).

(1) 2-[N-(4-Chlorobenzyl)-N-methylamino]ethyl ester of 5-ethoxycarbonyl-4-(2-trifluoromethylphenyl)-6-formyl-2-methyl-1,4-dihydropyridine-3-carboxylic acid.

N.M.R.: $\delta$ppm (CDCl$_3$): 1.25 (3H, t, J=7 Hz), 2.18 (3H, s), 2.42 (3H, s), 2.60 (2H, t, J=6.5 Hz), 3.45 (2H, s), 3.9–4.4 (4H, m), 5.70 (1H, broad s), 6.95 (1H, broad s), 7.2–7.7 (8H, m), 10.26 (1H, s).

(2) 2-Benzylthioethyl ester of 4-(2-cyanophenyl)-5-ethoxycarbonyl-6-formyl-2-methyl-1,4-dihydropyridine-3-carboxylic acid.

N.M.R.: $\delta$ppm (CDCl$_3$): 1.28 (3H, t, J=7 Hz), 2.43 (3H, s), 2.64 (2H, t, J=7 Hz), 3.68 (2H, s), 4.21 (2H, t, J=7 Hz), 4.26 (2H, q, J=7 Hz), 5.48 (1H, s), 7.01 (1H, broad s), 7.1–7.7 (9H, m), 10.51 (1H, s).

(3) 2-Phenylthioethyl ester of 4-(2-cyanophenyl)-5-ethoxycarbonyl-6-formyl-2-methyl-1,4-dihydropropyridine-3-carboxylic acid, mp 108°–110° C.

(4) 2-Ethylthioethyl ester of 5-ethoxycarbonyl-4-(2-trifluoromethylphenyl)-6-formyl-2-methyl-1,4-dihydropyridine-3-carboxylic acid.

N.M.R.: $\delta$ppm (CCl$_4$): 1.0–1.5 (6H, m), 2.1–2.7 (4H, m), 3.8–4.3 (4H, m), 5.5–5.65 (1H, m), 6.8–6.9 (1H, m), 7.0–7.7 (4H, m), 10.22 (1H, s).

EXAMPLE 13

The following compounds were obtained in substantially the same manner as that of Example 3-1).

(1) 2-[N-(4-chlorobenzyl)-N-methylamino]ethyl ester of 6-cyano-5-ethoxycarbonyl-4-(2-trifluoromethylphenyl)-2-methyl-1,4-dihydropyridine-3-carboxylic acid hydrochloride, mp 226°-227° C. (dec.).

IR$_{max}^{Nujol}$: 3190, 2700-2400, 2270, 1711, 1700, 1380, 1320, 1318, 1310, 1279, 1215, 1165, 1130, 1106, 1038, 726 cm$^{-1}$.

(2) 2-Benzylthioethyl ester of 6-cyano-4-(2-cyanophenyl)-5-ethoxycarbonyl-2-methyl-1,4-dihydropyridine-3-carboxylic acid.

N.M.R.: δppm (CDCl$_3$): 1.25 (3H, t, J=7 Hz), 2.36 (3H, s), 2.50 (2H, t, J=6 Hz), 3.66 (2H, s), 4.18 (2H, t, J=6 Hz), 4.23 (2H, q, J=7 Hz), 5.40 (1H, s), 7.2-7.7 (10H, m).

(3) 2-Phenylthioethyl ester of 6-cyano-4-(2-cyanophenyl)-5-ethoxycarbonyl-2-methyl-1,4-dihydropyridine-3-carboxylic acid, mp 126°-128.5° C.

(4) 2-Ethylthioethyl ester of 6-cyano-5-ethoxycarbonyl-4-(2-trifluoromethylphenyl)-2-methyl-1,4-dihydropyridine-3-carboxylic acid, mp 81°-82° C.

EXAMPLE 14

The following compounds were obtained in substantially the same manner as that of Example 4-1).

(1) 2-Benzylthioethyl ester of 4-(2-cyanophenyl)-5-ethoxycarbonyl-6-hydroxymethyl-2-methyl-1,4-dihydropyridine-3-carboxylic acid, mp 121°-122° C.

(2) 2-Phenylthioethyl ester of 4-(2-cyanophenyl)-5-ethoxycarbonyl-6-hydroxymethyl-2-methyl-1,4-dihydropyridine-3-carboxylic acid, mp 114°-116° C.

(3) 2-Ethylthioethyl ester of 5-ethoxycarbonyl-4-(2-trifluoromethylphenyl)-6-hydroxymethyl-2-methyl-1,4,-dihydropyridine-3-carboxylic acid.

N.M.R.: δppm (CDCl$_3$): 1.15 (3H, t, J=6 Hz), 1.23 (3H, t, J=6.25 Hz), 2.3-3.2 (4H, m), 2.65 (1H, t, J=6.25 Hz), 2.35 (3H, s), 3.8-4.6 (2H, m), 4.17 (2H, t, J=6.25 Hz), 4.77 (2H, s), 5.7-5.8 (1H, m), 7.1-7.8 (5H, m).

EXAMPLE 15

(1) A mixture of 2-ethylthioethyl 2-(2-trifluoromethylphenyl)acetoacetate (14.43 g) and ethyl 3-amino-4,4-diethoxycrotonate (9.56 g) was gradually heated untill 110° C. in the course of an hour and for additional 22 hours at the same temperature. To the reaction mixture was added ethyl acetate, washed twice with water and evaporated to dryness under reduced pressure to give an oil (16.4 g). This oil was chromatographed over silica gel (about 500 g) with a mixture of benzene and ethyl acetate (70:1, and then 25:1) and then chloroform as an eluent to give crude 2-ethylthioethyl ester of 5-ethoxycarbonyl-6-diethoxymethyl-4-(2-trifluoromethylphenyl)-2-methyl-1,4-dihydropyridine-3-carboxylic acid.

N.M.R.: δppm (CCl$_4$): 1.0-1.5 (12H, m), 2.3-2.8 (4H, m), 2.41 (3H, s), 3.4-4.5 (8H, m), 5.5-5.6 (1H, m), 6.13 (1H, s), 6.55 (1H, s), 7.1-7.7 (4H, m).

The following compounds were obtained in substantially the same manner as that of Example 15-1).

(2) 2-Ethylthioethyl ester of 5-ethoxycarbonyl-6-diethoxymethyl-4-(2-cyanophenyl)-2-methyl-1,4-dihydropyridine-3-carboxylic acid.

N.M.R.: δppm (CDCl$_3$): 1.23 (12H, t, J=7.5 Hz), 2.36 (3H, s), 2.58 (2H, t, J=7.5 Hz), 2.63 (2H, q, J=7.5 Hz), 3.4-3.9 (4H, m), 4.13 (2H, q, J=7.5 Hz), 4.19 (2H, t, J=7.5 Hz), 5.37 (1H, s), 6.22 (1H, s), 6.80 (1H, broad s), 7.3-7.7 (4H, m).

(3) 2-Benzylthioethyl ester of 5-ethoxycarbonyl-6-diethoxymethyl-4-(2-cyanophenyl)-2-methyl-1,4-dihydropyridine-3-carboxylic acid.

| N.M.R. δppm (CDCl$_3$): | 1.26 | (9H, t, J = 7Hz), | |
|---|---|---|---|
| | 2.38 | (3H, s), 2.64 | (2H, t, |
| | J = 7Hz), | 3.5-4.0 (m) | ⎫ |
| | | | ⎬ (6H), |
| | | 3.7 (s) | ⎭ |
| | 4.15 | (4H, q, J = 7Hz), | |
| | 5.39 | (1H, s), 6.27 | (1H, s), |
| | 6.85 | (1H, broad s), | |
| | 7.1-7.7 | (9H, m) | |

(4) 2-Phenylthioethyl ester of 5-ethoxycarbonyl-6-diethoxymethyl-4-(2-cyanophenyl)-2-methyl-1,4-dihydropyridine-3-carboxylic acid.

N.M.R.: δppm (CDCl$_3$): 1.22 (9H, t, J=7 Hz), 2.33 (3H, s), 3.11 (2H, t, J=7.5 Hz), 3.4-3.9 (4H, m), 4.07 (2H, t, J=7.5 Hz), 4.15 (2H, q, J=7 Hz), 5.33 (1H, s), 6.22 (1H, s), 6.81 (1H, broad s), 7.1-7.7 (9H, m).

(5) Isopropyl ester of 4-(2-biphenylyl)-5-methoxycarbonyl-6-dimethoxymethyl-2-methyl-1,4-dihydropyridine-3-carboxylic acid, mp 103°-108° C. was obtained by reacting isopropyl 3-aminocrotonate and methyl 2-(2-biphenylylmethylene)-4,4-dimethoxyacetoacetate, which was prepared according to the same manner to that of Preparation (1), in substantially the same manner to that of Example 15-1).

What is claimed is:

1. A compound of the formula:

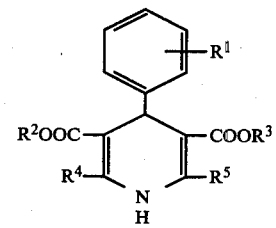

wherein $R^1$ is nitro, halogen, cyano, trihalo(lower)alkyl or phenyl, $R^2$ is lower alkyl; [N-lower alkyl-N-mono or di halophenyl(lower)alkyl]amino(lower)alkyl; [N-lower alkyl-N-lower alkylphenyl(lower)alkyl]amino(lower)alkyl; [N-lower alkyl-N-lower alkoxyphenyl(lower)alkyl]amino(lower)alkyl; phthalimido(lower)alkyl; lower alkanoyloxy(lower)alkyl; lower alkylthio(lower)alkyl, phenyl(lower)alkylthio(lower)alkyl; or phenylthio(lower)alkyl;

$R^3$ and $R^4$ are each lower alkyl, and $R^5$ is cyano or 2-cyanovinyl with a proviso that when $R^1$ is nitro, halogen, cyano or trihalo(lower)alkyl and $R^2$ is lower alkyl, $R^3$ and $R^4$ is lower alkyl, then $R^5$ is 2-cyanovinyl, and pharmaceutically acceptable salts thereof.

2. A compound according to claim 1, wherein
$R^1$ is nitro, cyano or trihalo(lower)alkyl,
$R^2$ is [N-lower alkyl-N-mono- or dihalophenyl(lower)alkyl]amino(lower)alkyl, and
$R^5$ is cyano.

3. A compound according to claim 2, wherein
$R^2$ is [N-lower alkyl-N-mono- or dihalobenzyl]amino(lower)alkyl.

4. A compound according to claim 3, wherein
$R^1$ is 3-nitro, 2-cyano or 2-trifluoromethyl,
$R^2$ is 2-(N-methyl-N-4-mono- or 3,4-dichlorobenzylamino)ethyl,
$R^3$ is ethyl, and
$R^4$ is methyl.

5. A compound according to claim 4, wherein
$R^1$ is 3-nitro,
$R^2$ is 2-(N-methyl-N-4-chlorobenzylamino)ethyl, and its hydrochloride.

6. A compound according to claim 4, wherein
$R^1$ is 3-nitro,
$R^2$ is 2-(N-methyl-N-3,4-dichlorobenzylamino)ethyl, and its hydrochloride.

7. A compound according to claim 4, wherein
$R^1$ is 2-cyano,
$R^2$ is 2-(N-methyl-N-4-chlorobenzylamino)ethyl, and its hydrochloride.

8. A compound according to claim 4, wherein
$R^1$ is 2-cyano,
$R^2$ is 2-(N-methyl-N-3,4-dichlorobenzylamino)ethyl, and its hydrochloride.

9. A compound according to claim 4, wherein
$R^1$ is 2-trifluoromethyl,
$R^2$ is 2-(N-methyl-N-4-chlorobenzylamino)ethyl, and its hydrochloride.

10. A compound according to claim 4, wherein
$R^1$ is 2-trifluoromethyl,
$R^2$ is 2-(N-methyl-N-3,4-dichlorobenzylamino)ethyl, and its hydrochloride.

11. A compound according to claim 1, wherein
$R^1$ is nitro, cyano, trihalo(lower)alkyl or phenyl,
$R^2$ is lower alkyl, [N-lower alkyl-N-lower alkylphenyl(lower)alkyl]amino(lower)alkyl, [N-lower alkyl-N-lower alkoxyphenyl(lower)alkyl]amino(lower)alkyl, phthalimido(lower)alkyl, lower alkanoyloxy(lower)alkyl, lower alkylthio(lower)alkyl, phenyl(lower)alkylthio(lower)alkyl or phenylthio(lower)alkyl, and
$R^5$ is cyano.

12. A compound according to claim 1, wherein
$R^1$ is halogen,
$R^2$ is lower alkyl, $R^3$ and $R^4$ are lower alkyl and
$R^5$ is 2-cyanovinyl.

13. A pharmacuetical composition for treatment of cardiovascular disease or hypertension comprising an effective amount of the compound of claim 1 in association with a non-toxic, pharmaceutically acceptable carrier or excipient.

* * * * *